(12) United States Patent
Ford et al.

(10) Patent No.: US 8,900,627 B2
(45) Date of Patent: Dec. 2, 2014

(54) COMPOSITIONS FOR THE IN VIVO DELIVERY OF RNAI AGENTS

(75) Inventors: Lance Ford, Austin, TX (US); David Brown, Austin, TX (US); Andreas G. Bader, Austin, TX (US)

(73) Assignees: Mirna Therapeutics, Inc., Austin, TX (US); BIOO Scientific Corporation, Austin, TX (US)

( * ) Notice: Subject to any disclaimer, the term of this patent is extended or adjusted under 35 U.S.C. 154(b) by 209 days.

(21) Appl. No.: 12/479,747

(22) Filed: Jun. 5, 2009

(65) Prior Publication Data

US 2009/0306194 A1    Dec. 10, 2009

Related U.S. Application Data

(60) Provisional application No. 61/059,620, filed on Jun. 6, 2008, provisional application No. 61/092,569, filed on Aug. 28, 2008.

(51) Int. Cl.
| | | |
|---|---|---|
| *A61K 9/127* | (2006.01) | |
| *C07H 21/02* | (2006.01) | |
| *C07H 21/04* | (2006.01) | |
| *C12N 15/11* | (2006.01) | |

(52) U.S. Cl.
USPC ...... 424/450; 536/24.35; 536/23.1; 514/44 A; 514/938

(58) Field of Classification Search
None
See application file for complete search history.

(56) References Cited

U.S. PATENT DOCUMENTS

| | | | |
|---|---|---|---|
| 4,610,868 A | 9/1986 | Fountain et al. | |
| 5,417,978 A | 5/1995 | Tari et al. | |
| 5,422,120 A | 6/1995 | Kim | |
| 5,766,627 A | 6/1998 | Sankaram et al. | |
| 5,855,911 A | 1/1999 | Lopez-Berestein et al. | |
| 5,962,016 A | 10/1999 | Willis | |
| 6,042,846 A | 3/2000 | Lopez-Berestein et al. | |
| 6,071,534 A | 6/2000 | Kim et al. | |
| 6,074,667 A | 6/2000 | Kinnunen et al. | |
| 6,120,794 A * | 9/2000 | Liu et al. ........................ 424/450 |
| 6,132,766 A | 10/2000 | Sankaram et al. | |
| 6,258,377 B1 | 7/2001 | New et al. | |
| 6,287,591 B1 | 9/2001 | Semple et al. | |
| 6,290,987 B1 | 9/2001 | Modi | |
| 6,361,791 B1 | 3/2002 | Huang et al. | |
| 6,429,200 B1 | 8/2002 | Monahan et al. | |
| 6,458,382 B1 | 10/2002 | Herweijer et al. | |
| 6,534,483 B1 | 3/2003 | Bruno et al. | |
| 6,743,779 B1 | 6/2004 | Unger et al. | |
| 6,977,244 B2 | 12/2005 | Tormo et al. | |
| 7,112,337 B2 | 9/2006 | Huang et al. | |
| 7,192,605 B2 | 3/2007 | Herweijer et al. | |
| 7,220,853 B2 | 5/2007 | Lopez-Berestein et al. | |
| 7,285,288 B1 | 10/2007 | Tormo et al. | |
| 7,371,404 B2 | 5/2008 | Panzner et al. | |
| 7,888,010 B2 | 2/2011 | Brown et al. | |
| 8,071,562 B2 | 12/2011 | Bader et al. | |
| 8,173,611 B2 | 5/2012 | Brown et al. | |
| 2003/0133988 A1* | 7/2003 | Fearon et al. ................ 424/493 |
| 2004/0037874 A1 | 2/2004 | Hong et al. | |
| 2004/0142025 A1 | 7/2004 | MacLachlan et al. | |
| 2004/0146551 A1 | 7/2004 | Mannino et al. | |
| 2005/0064595 A1 | 3/2005 | MacLachlan et al. | |
| 2006/0134221 A1* | 6/2006 | Geall ............................ 424/489 |
| 2006/0159737 A1 | 7/2006 | Panzner et al. | |
| 2007/0104775 A1 | 5/2007 | Panzner et al. | |
| 2007/0123482 A1* | 5/2007 | Stoffel et al. .................... 514/44 |
| 2007/0202157 A1 | 8/2007 | Lopez-Berestein et al. | |
| 2007/0243132 A1* | 10/2007 | Russell-Jones et al. ..... 424/1.11 |
| 2008/0063701 A1 | 3/2008 | Keller et al. | |
| 2008/0181938 A1 | 7/2008 | Kaspar | |
| 2008/0206341 A1 | 8/2008 | Gasco | |
| 2008/0306153 A1 | 12/2008 | Panzner et al. | |
| 2008/0311181 A1 | 12/2008 | Endert et al. | |
| 2009/0011003 A1 | 1/2009 | Yamauchi et al. | |
| 2009/0012021 A1 | 1/2009 | Sood et al. | |
| 2009/0176725 A1* | 7/2009 | Morrissey et al. ............. 514/44 |
| 2009/0227533 A1 | 9/2009 | Bader et al. | |

FOREIGN PATENT DOCUMENTS

| | | |
|---|---|---|
| EP | 1 096 921 B1 | 4/2003 |
| EP | 1611879 | 1/2006 |
| JP | 2008 115101 | 5/2008 |
| WO | WO 98/33932 | 8/1998 |
| WO | WO 00/06120 | 2/2000 |
| WO | WO 2006/113679 | 10/2006 |
| WO | WO 2007 070983 | 6/2007 |
| WO | WO 2008/109432 | 9/2008 |
| WO | WO 2008 137758 | 11/2008 |
| WO | WO 2009/002719 | 12/2008 |

OTHER PUBLICATIONS

International Search Report and Written Opinion dated Feb. 5, 2010, issued in PCT/US2009/046505.

Bennett et al., "Cationic Lipids Enhance Cellular Uptake and Activity of Phosphorothioate Antisense Oligonucleotides," *Molecular Pharmacology* 41:1023-1033 (1992).

Bioo Scientific Catalog, "MaxSuppressor™, In Vivo RNA LANCEr", In Vivo RNAi, Catalog #3407, copyright 2008, visited at http://www.biooscientific.com/catalog/In_Vivo_RNA-LANCEr.htm on May 7, 2009, 2 pages.

Bioo Scientific Catalog, "MaxSuppressor™, In Vivo RNA LANCEr II", In Vivo RNAi, Catalog #3410-01, copyright 2008, visited at http://www.biooscientific.com/catalog/In_Vivo_RNA-LANCEr_II.htm on May 7, 2009, 2 pages.

(Continued)

*Primary Examiner* — Richard Schnizer
(74) *Attorney, Agent, or Firm* — Nutter McClennen & Fish LLP; Konstantin Linnik; Isaac A. Hubner

(57) ABSTRACT

This application describes emulsion formulations containing neutral phospholipids for delivering RNAi, anti-miRNA, or aptamer agents in vivo. The application also relates to methods of making the formulations, and uses of the formulations as delivery agents.

29 Claims, 17 Drawing Sheets

(56) References Cited

OTHER PUBLICATIONS

Campbell, "Toxicity of Some Charged Lipids used in Liposome Preparations," *Cytobios* 37:21-26 (1983).

Chung et al., "Oil Components Modulate Physical Characteristics and Function of the Natural Oil Emulsions as Drug or Gene Delivery System," *Journal of Controlled Release* 71:339-350 (2001).

Ferrari et al, "Synergy Between Cationic Lipid and Co-Lipid Determines the Macroscopic Structure and Transfection Activity of Lipoplexes," *Nucleic Acids Research* vol. 30, No. 8 1808-1816 (2002).

Filion et al., "Toxicity and immunomodulatory activity of liposomal vectors formulated with cationic lipids toward immune effector cells," *Biochimica et Biophysica Acta* 1329:245-256 (1997).

Gutiérrez-Puente et al. Safety, Pharmacokinetics, and Tissue Distribution of Liposomal P-Ethoxy Antisense Oligonucleotides Targeted to Bcl-2[1], *The Journal of Pharmacology and Experimental Therapeutics* 291:865-869 (1999).

Hassani et al. "Lipid-Mediated siRNA Delivery Down-Regulates Exogenous Gene Expression in the Mouse Brain at Picomolar Levels," *The Journal of Gene Medicine* 7:198-207 (2005).

Kim et al. Optimization of Lipid Composition in Cationic Emulsion as In Vitro and In Vivo Transfection Agents, *Pharamaceutical Research*, vol. 18, No. 1 (2001).

Kim et al., "The Effects of Serum on the Stability and the Transfection Activity of the Cationic Lipid Emulsion with Various Oils," *International Journal of Pharmaceuticals* 252:241-252 (2003).

Landen Jr. et al. "Therapeutic EphA2 Gene Targeting In Vivo Using Neutral Liposomal Small Interfering RNA Delivery," *Cancer Res* 2005 65:15 (2005).

Miller et al. "Liposome-Cell Interactions in Vitro: Effect o Liposome Surface Charge on the Binding and Endocytosis of Conventional and Sterically Stabilized Liposomes," *Biochemistry* 37:12875-12883 (1998).

Nicolau et al. "Liposomes as Carriers for in Vivo Gene Transfer and Expression" *Methods in Enzymology*, vol. 149 (1987).

Senior et al., "Interaction of positively-charged liposomes with blood: implications for their application in vivo," *Biochimica et Biophysica Acta* 1070:173-179 (1991).

Sørensen et al. "Gene Silencing by Systemic Delivery of Synthetic siRNAs in Adult Mice," *J. Mol. Biol.*, 327:761-766 (2003).

Wang et al., A Novel Procedure for Preparation of Submicron Liposomes-Lyophilizaton of Oil-in Water Emulsions, *Journal of Liposome Research*, 1-10 (2009).

Whittenton et al. "Evaluation of Asymmetric Liposomal Nanoparticles for Encapsulation of Polynucleotides," *Langmuir* 24:8533-8540 (2008).

Wong et al. "Appearance of β-Lactamase Activity in Animal Cells Upon Liposome-Mediated Gene Transfer," *Gene* 10:87-94 (1980).

Bitko et al., Inhibition of respiratory viruses by nasally administered siRNA. Nat Med. Jan. 2005;11(1):50-5. Epub Dec. 26, 2004

Griffiths-Jones, Nucleic Acids Research, 2004, 32, Database Issue, D109-D111.

Griffiths-Jones et al., Nucleic Acids Research, 2006, 34, Database Issue, D140-D144.

Griffiths-Jones et al., Nucleic Acids Research, 2008, 36, Database Issue, D154-D158.

\* cited by examiner

COMPOSITIONS FOR THE IN VIVO DELIVERY OF RNAI AGENTS

This application claims the benefit of priority of U.S. Provisional Application No. 61/059,620, filed Jun. 6, 2008, and U.S. Provisional Application No. 61/092,569, filed Aug. 28, 2008.

Many types of nucleic acids are currently being investigated as possible therapeutics, such as RNA interference agents, aptamers, anti-miRNAs, or gene replacement therapy. RNA interference (RNAi) typically relates to a cellular pathway that regulates gene expression, primarily at the post-transcriptional level. Scientists use a variety of RNAi agents and tools to perform functional genomic screening, drug discovery studies and in vivo target validation, and RNAi agents can down-regulate a gene's expression in in vitro and in vivo assays. Examples of RNAi agents include, but are not limited to, short interfering RNA (siRNA), micro-RNA (miRNA), Piwi-interacting RNAs (piRNAs), ribozymes and antisense compounds. Many RNAi agents work through a common pathway, and typically result in cleavage, reduced translation, or other interference with expression of one or more target mRNA molecules (FIG. 1).

MicroRNAs (miRNAs) are a class of endogenous small non-coding RNAs that regulate gene expression by binding to target mRNA transcripts and (1) initiating transcript degradation or (2) altering protein translation from the transcript. miRNAs are frequently differentially expressed in cancer tissues and other diseased tissues and—when deregulated—contribute to the development of various human diseases, including cancer. Anti-miRNAs are short nucleic acids that interfere with the activity of a target miRNA by hybridization. Instead of reducing the expression or activity of a target mRNA, use of an anti-miRNA results in increased activity of the mRNA(s) regulated by the target miRNA.

The RNAi agent can enter the RNAi pathway starting from within the cells, or it can be delivered into cells. Although RNAi agents are being developed as gene-specific medicines, the future success of the technology is intimately tied to the development of delivery chemistries, methods, and formulations that are non-toxic and efficient at delivering RNAi agents into cells and organs in live plants and animals.

Aptamers are small nucleic acid molecules that bind specifically to molecular targets such as proteins. Unlike nucleic acid therapeutics that act by hybridizing to another nucleic acid target, aptamers form three-dimensional shapes that allow for specific binding to enzymes, growth factors, receptors, viral proteins, and immunoglobulins.

Efficient delivery into target organs and the high costs associated with such delivery is one of the main limitations facing therapeutic applications for oligonucleotide-based agents. For example, the amount of siRNA used per injection in an average sized mouse currently ranges from 0.03 to 2.4 mg per dose (1-50 mg/kg). An average human weighs about 80 kg and proportionately would require about 0.08 to 4.0 g of siRNA. Currently, 0.08 g of research grade siRNA costs over $3000. The costs of nucleic acids for pharmaceuticals, which incorporate the costs of regulatory drug approval and testing requirements, will be significantly greater. Similar problems have been faced for other antisense compounds and oligonucleotide-based medicines. Thus, increasing the efficiency of uptake into target cells, or improving stability of the RNAi formulations, for example, will decrease the amount of RNAi agent needed for treatment, both decreasing costs and the potential for damaging side effects. There is a need for improved RNAi reagent compositions for the treatment of disease and also for processes to make such compositions.

Liposomes and emulsions made from cationic phospholipids have previously been used for delivery and transfection of small molecules and nucleic acids. In these formulations, the cationic lipids and the negatively charged nucleic acids form a complex through electrostatic interactions. However, these formulations often have toxicity profiles that make them unsuitable for in vivo applications. (See, e.g., Campbell P I., *Cytobios.* 37(145):21-6 (1983); Senior J H et al., *Biochim Biophys Acta.* 1070(1):173-9 (1991); Filion M C et al., *Biochim BiophysActa.* 1329(2):345-56 (1997).

The present invention relates to lipophilic formulations of RNAi reagents, anti-miRNAs, or aptamers. The formulations can be called a phospholipid-oil-RNAi emulsion (PORE), containing a neutral phospholipid, an oil, and an RNAi agent (FIG. 2). In some embodiments, the formulations include a non-ionic surfactant, a lipid component, and an aqueous component for delivery of an RNAi agent, anti-miRNA, or aptamer. Methods for making such formulations and using the formulations for therapeutic purposes are also described herein. These approaches have utility for advancing the therapeutic application of RNAi agents and the ability of RNAi agents to be delivered in vivo (FIG. 3).

In some embodiments, an emulsion formulation contains a neutral phospholipid, an oil, and a non-ionic surfactant. In other embodiments, more than one neutral phospholipid is used in the formulation. In additional embodiments, more than one oil is used in the formulation. In certain embodiments, the neutral phospholipid is 1,2-dioleoyl-sn-glycero-3-phosphocholine (DOPC). In some embodiments, the oil is squalene. In additional embodiments, polysorbate 20 (Tween 20) or polysorbate 80 (Tween 80) is the non-ionic surfactant. In certain embodiments, the RNAi agent is a miRNA or an siRNA. The emulsion formulation may include additional components such as antioxidants, waxes, detergents, or combinations thereof. Certain embodiments include methods of preparing emulsion formulations. In some embodiments, a lipid component is prepared and mixed with an aqueous component to form an emulsion.

The emulsion formulations may be used to deliver at least one RNAi agent, anti-miRNA agent, or aptamer to tissues in a living animal. In certain embodiments the emulsion formulation protects the RNAi agent from degradation in the circulatory system. In addition, the emulsion formulation can facilitate the transfer of the RNAi agent across physiological barriers such as cell membranes.

In one embodiment, a method of treating diseases in mammals or modulating expression of a target nucleic acid in a cell includes administering a formulation containing an RNAi agent, an anti-miRNA, or an aptamer to a mammalian subject in an amount effective for relieving some symptoms of the disease or changing the level of target nucleic acid in the cell. In some embodiments, the compositions and methods may be used to treat diseases and disorders characterized by the expression or over-expression of a gene or group of genes, such as cancer, metabolic diseases, infectious diseases, and immune disorders, among others.

Other embodiments of the invention are discussed throughout this application. Other objects, features, and advantages of the present invention will become apparent from the following detailed description. Any embodiment discussed with respect to one aspect of the invention applies to other aspects of the invention as well and vice versa. The embodiments in the Examples section are understood to be embodiments of the invention that are applicable to all aspects of the invention.

It should be understood, however, that the detailed description and the specific examples, while indicating specific embodiments of the invention, are given by way of illustration only, since various changes and modifications within the spirit and scope of the invention will become apparent to those skilled in the art from this detailed description.

Additional aspects of the invention are set forth in the description that follows.

EXEMPLARY EMBODIMENTS

Figure 1:
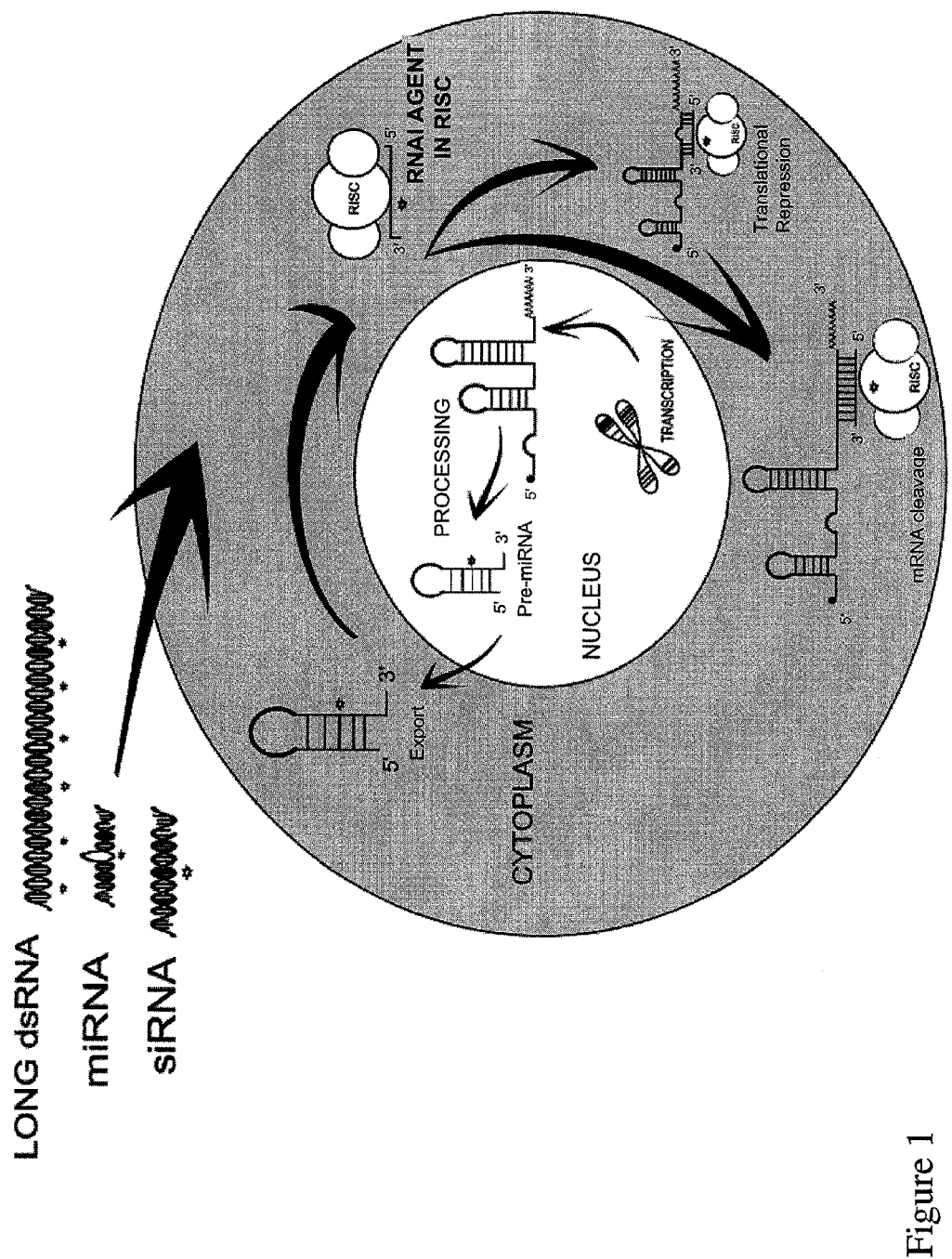
FIG. 1 outlines the cellular pathway for producing RNAi and a RNAi-mediated mechanism for silencing gene expression at the post-transcriptional level.
Figure 2:
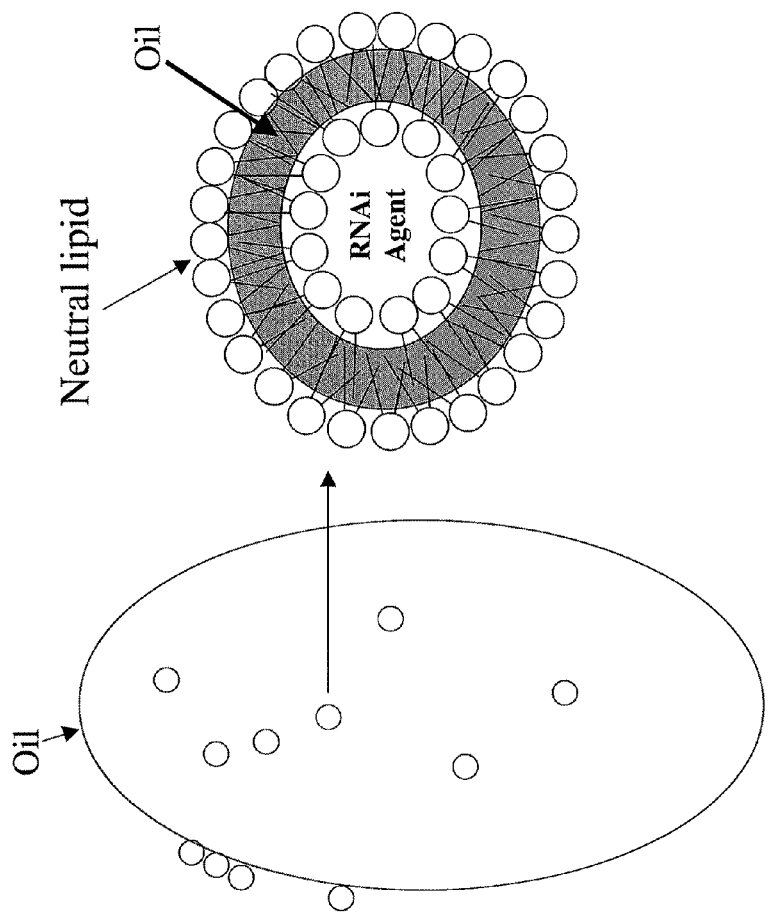
FIG. 2 is a depiction of a phospholipid-oil-RNAi emulsion (PORE) at the microscopic level.
Figure 2:
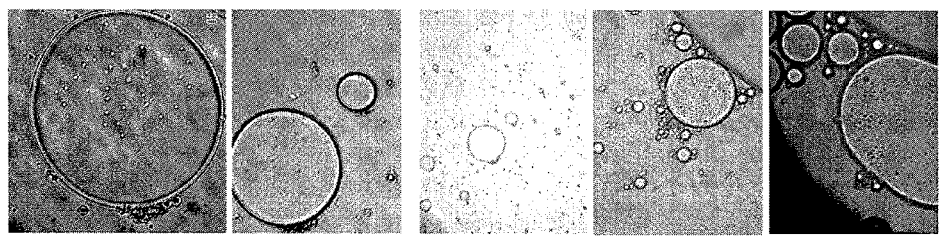
Figure 3:
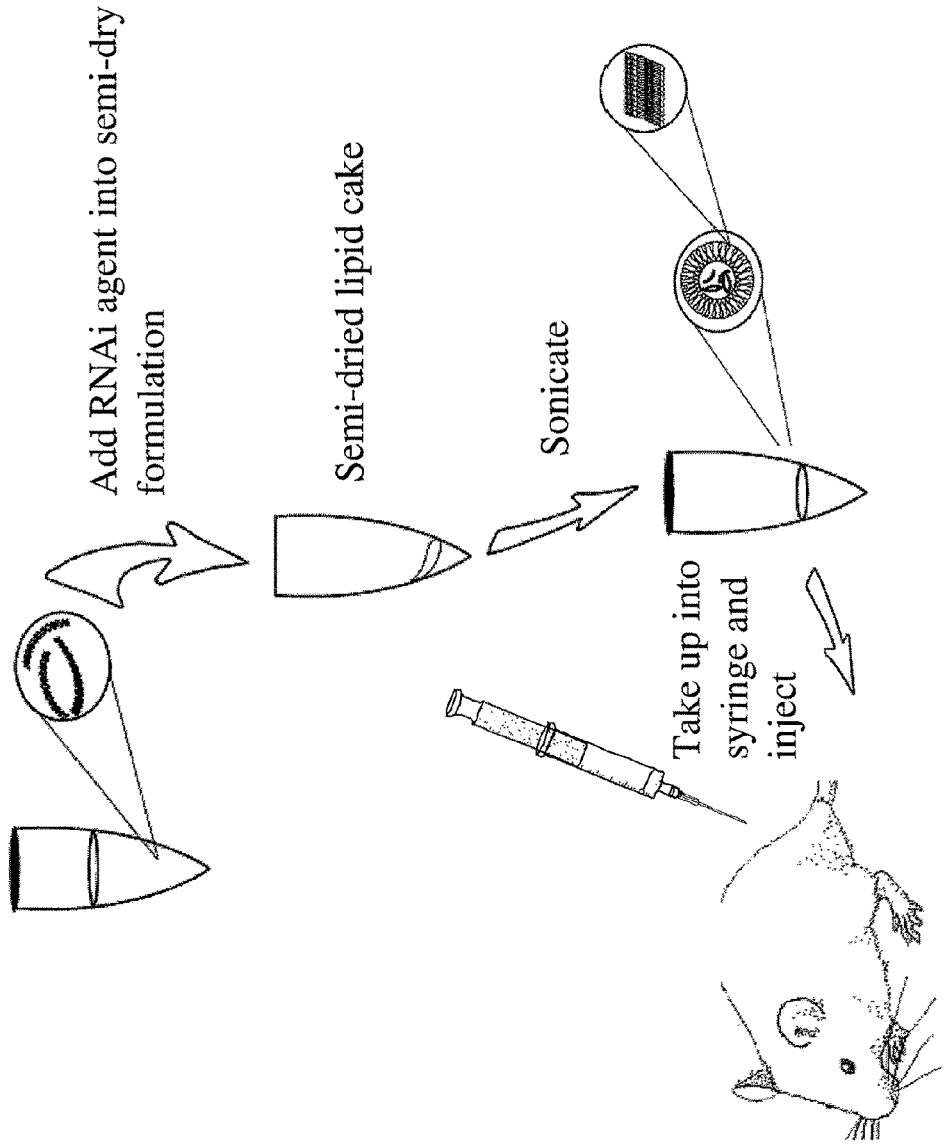
FIG. 3 outlines a method for producing PORE and its use in vivo.

In certain aspects, the emulsion formulations contain neutral phospholipids and oils for delivering RNAi agents to cells. In certain aspects, the emulsion formulations contain polysorbate and a neutral phospholipid for delivering RNAi agents to cells. In some aspects, the RNAi formulations are used to treat diseases in animals or humans. Methods of making and using the RNAi formulations are included.

To assist in understanding the present invention, certain terms are first defined. Additional definitions are provided throughout the application.

The term "RNAi agent" includes short interfering RNA (siRNA), micro-RNA (miRNA), Piwi-interacting RNAs (piRNAs), ribozymes and antisense compounds. RNAi agents include nucleic acids that include RNA, DNA, or both. In some embodiments, the RNAi agent is less than 200 nucleotides in length. In other embodiments, the RNAi agent is less than 50 nucleotides in length. In certain embodiments, the RNAi agent is about 15 to about 25 nucleotides in length. In some embodiments, the RNAi agent is double-stranded, while other embodiments include single-stranded RNAi agents. RNAi agents may be chemically modified.

As used herein, the term "siRNA" refers to double-stranded RNAs of about 15 to about 25 nucleotides in length. siRNAs may have blunt ends, or may have single-stranded overhangs on one or both ends. In addition, siRNAs may include chemical modifications such as backbone, sugar, base, or terminal (3' or 5' end) modifications. siRNAs may contain sequences that are fully or partially complementary to target mRNA(s).

As used herein, the term "microRNA" (miRNA) includes human miRNAs, mature single stranded miRNAs, precursor miRNAs, and variants thereof, which may be naturally occurring or synthetically produced. In some instances the term "miRNA" also includes primary miRNA transcripts and duplex miRNAs. The term "mature," when modifying miRNA or a specific miRNA such as miR-103, refers to the mature sequence(s) processed from the corresponding pre-miRNA sequence that are present in a biological sample. The prefix "hsa", when used with a specific miRNA (e.g., hsa-miR-34a), refers to a human miRNA sequence. The sequences for particular miRNAs, including human mature and precursor sequences, are reported in the miRBase::Sequences Database Nucleic Acids Research, 2008, 36, Database Issue, D154-D158; Griffiths-Jones et al., Nucleic Acids Research, 2006, 34, Database Issue, D140-D144; Griffiths-Jones, Nucleic Acids Research, 2004, 32, Database Issue, D109-D111). The skilled artisan will appreciate that scientific consensus regarding the precise nucleic acid sequence for a given miRNA, in particular for mature forms of the miRNAs, may change with time.

"Emulsion", as used herein, means small, insoluble lipid droplets suspended in an aqueous solution. The lipid droplets may contain oil, phospholipid, surfactant, or mixtures thereof.

The use of the word "a", "an" or "the" when used in conjunction with the term "comprising" in the claims and/or the specification may mean "one," but it is also consistent with the meaning of "one or more," "at least one," and "one or more than one."

I. EMULSION FORMULATIONS

In certain embodiments, an emulsion formulation that includes a lipid component, an aqueous component, and a non-ionic surfactant may be used to deliver an RNAi agent to tissues in a living animal. In some embodiments, the average diameter of the lipid droplets in the emulsion is between 50 and 2,000 nm. In other embodiments, the average diameter is between 50-100, 100-150, 150-200, 200-300, 300-400, 400-500, 500-600, 100-500, 100-1000, 500-1000, or 1000-2000. One of skill in the art will understand that emulsion preparations contain lipid particles with a range of sizes. In some embodiments, an emulsion preparation contains lipid particles that vary 10, 15, 20, or 25% from the average particle size. In some embodiments, the lipid droplets will be found in a larger lipid sphere. In certain embodiments, the lipid sphere will have a diameter from about 10 µm to about 1000 µm. Those of skill in the art will recognize that different tissues may require different particle sizes for delivery. For example, the nature of the vasculature in different tissues or tumors may affect the particle size for optimal delivery.

A. Lipid Component

The lipid component of the formulation contains a neutral phospholipid. In some embodiments, the lipid component also contains an oil or wax. The lipid component may contain from 20-100% neutral phospholipid and 0-80% oil or wax by weight. In formulations with oil or wax, the ratio of neutral phospholipid to oil or wax in the formulation may be from 1:2 to 1:6 by weight. In some embodiments, the phospholipid:oil ratio is about 1:2, 1:3, 1:4, 1:5, or 1:6.

1. Phospholipids

Phospholipids are bipolar molecules comprised most commonly of a glycerol molecule bonded to two fatty acids and a phosphate group. In some phospholipids, the phosphate group is bonded to another chemical group, called the head group. If the net charge of the phospholipid is zero, then it is a neutral phospholipid. Phospholipids with net positive charge are cationic phospholipids, and those with net negative charge are anionic phospholipids.

In some embodiments, the phospholipid is a neutral phospholipid. Neutral phospholipids include, but are not limited to, phosphatidylcholine (PC), 1,2-Dioleoyl-sn-glycero-3-phosphocholine (DOPC), lecithin, phosphatidylethanolamine (PE), lysolecithin, lysophosphatidylethanolamine, sphinogomyelin (SM), cardiolipin, phosphosphatidic acid, 1,2-Distearoyl-sn-glycero-3-phosphocholine (DSPC), 1,2-Dipalmitoyl-sn-glycero-3-phosphoethanolamine (DPPE), 1-Palmitoyl-2-oleoyl-sn-glycero-3-phosphocholine (POPC), 1,2-Dilauroyl-sn-glycero-3-phosphocholine (DLPC), 1,2-Dimyristoyl-sn-glycero-3-phosphocholine (DMPC), 1,2-Dipalmitoyl-sn-glycero-3-phosphocholine (DPPC), 1,2-Dimyristoyl-sn-glycero-3-phosphoethanolamine (DMPE), 1,2-Dioleoyl-sn-glycero-3-phosphoethanolamine (DOPE), dipalmitoloeoyl-PE, diphytanoyl-PE, DSPE, dielaidoyl-PE, dilinoleoyl-SM, and dilinoleoyl-PE. In some embodiments, the neutral phospholipid DOPC and/or the neutral phospholipid DOPE is used in the emulsion formulation.

2. Oils and Waxes

"Oil", as used herein, refers to a heterogeneous group of neutral, flammable substances that are liquid at room temperature and are characteristically soluble in relatively non-polar solvents but only sparingly soluble in aqueous solvents. There are three main groups: (1) animal and vegetable oils, which include primarily triacylglycerols, but may also include varying amounts of fatty-acid esters of other alcohols; (2) mineral oils, derived from petroleum, coal, shale, which includes hydrocarbons; and (3) essential oils.

Examples of oils include, but are not limited to, vegetable oil, cottonseed oil, rapeseed oil, olive oil, mineral oil, sweet almond oil, castor oil, coconut oil, palm oil, hemp seed oil, flax oil, fish oil, whale blubber derived oils, shark liver oil, squalene, or squalene waxes. In additional embodiments, the oil may include oily fatty alcohols, esters of sorbitol and fatty acids, medium chain triglycerides, oily sucrose esters, or oil derived from any plant or animal source. In some embodiments, the oil may be an ionic or non-ionic block copolymer, styrene, divinylbenzene, butyl acrylate, 2-ethylhexyl acrylate, cyclohexyl acrylate, decyl acrylate, lauryl acrylate, dodecenyl acrylate, myristyl acrylate, palmityl acrylate, hexadecenyl acrylate, stearyl acrylate, octadecenyl acrylate, behenyl acrylate, butyl methacrylate, 2-ethylhexyl methacrylate, cyclohexyl methacrylate, decyl methacrylate, lauryl methacrylate, dodecenyl methacrylate, myristyl methacrylate, palmityl methacrylate, hexadecenyl methacrylate, straryl methacrylate, actadecenyl, methacrylate, or behenyl methacrylate. In some embodiments, squalene may be used to form an emulsion formulation.

In certain embodiments, the formulation contains a wax, either in place of or in addition to the oil. "Wax" is used herein to mean any lipid fraction from living organisms or from crude petroleum that is a plastic substance, hard when cold, easily molded when warm, and insoluble in water or any fatty-acid ester of a long-chain monohydroxyl alcohol.

Examples of waxes include, but are not limited to, beeswax, Stedmans wax, Chinese wax, Shellac wax, Spermaceti wax, Lanolin wax, Ear wax, Bayberry wax, Candelilla wax, castor wax, eapatro wax, japan wax, jojoba wax, ouricury wax, rice bran wax, ceresin wax, montan wax, ozocerite wax, peat wax, paraffin wax, microcrystalline wax, polyethylene wax, fisher-tropsch wax, chemically modified wax, substituted amide wax, or polymerized alpha olefins or combinations thereof.

B. Aqueous Component

The aqueous component of the emulsion formulation contains an RNAi agent, anti-miRNA agent, or aptamer in an aqueous medium. The aqueous component can be any pharmaceutically acceptable solution or buffer, such as phosphate buffered saline (PBS), saline, Ringer's solution, or water. Known buffering agents and systems can be included in a buffered aqueous component. In certain embodiments, the RNAi or anti-miRNA agent is in the aqueous solution at a concentration of about 0.1 mg/ml to about 20 mg/ml.

The RNAi agent includes, but is not limited to, short interfering RNA (siRNA), micro-RNA (miRNA), Piwi-interacting RNAs (piRNAs), ribozymes and antisense compounds. In some embodiments, the RNAi agent is siRNA or miRNA. In some embodiments, the RNAi agent is expressed from a plasmid or other expression vector. In other instances, RNAi agents are produced as PCR products. RNAi agents may be single or double-stranded, and some RNAi agents include hairpin or other secondary structures. Some RNAi agents include chemically-modified RNA or DNA, such as backbone, sugar, base, terminal (3'- or 5' end) modifications. RNAi agents can include anti-cancer agents, antiviral agents, antibacterial agents, immune-modulatory agents, anti-parasitic agents, as well as agents that modulate inflammation, metabolism, or other pathways that may be involved in disease or infection.

In some embodiments, the ratio of lipid component to RNAi agent is about 10:1, 20:1, 30:1, 40:1, 50:1 or 100:1 by weight. In additional embodiments, the ratio of the lipid component to the aqueous component is between 1:1 and 1:1000 by weight. In certain embodiments the lipid:aqueous ratio is about 1:1, 1:5, 1:10, 1:20, 1:50, 1:100, 1:500, or 1:1000 by weight.

C. Non-Ionic Surfactants

In some embodiments, the emulsion formulation includes a non-ionic surfactant. Examples of non-ionic surfactants include, but are not limited to, polysorbate 20 (Tween 20), polysorbate 80 (Tween 80), Nonidet P-40 (NP-40), CHAPS or combinations thereof. Additional examples of non-ionic surfactants include Triton X 100, Triton X 114, NP 40, Brij-35, Brij-58, octyl glucoside, and octylthio glucoside. In some embodiments, the surfactant Tween 20 may be used to form an emulsion formulation.

In certain embodiments, the non-ionic surfactant is between 0.01% and 50% of the total formulation by weight. In some embodiments, the surfactant is about 0.01, 0.1, 1, 5, 10, 20, 30, 40 or 50% of the total emulsion formulation by weight. In certain embodiments, the surfactant is about 0.1-5,1-10, 2-20, 10-33, 20-40, 20-33, 30-50, 30-40, or 40-50% of the total emulsion formulation by weight. In other embodiments, the ratio of surfactant to lipid component is between 1:10,000 and 1:3,000; 1:3,000 and 1:1,000; 1:1,000 and 1:300; 1:300 and 1:100; 1:100 and 1:10; 1:30 and 1:10; 1:30 and 1:1; 1:1 and 3:1; 1:1 and 10:1; 1:1 and 15:1; 15:1 and 30:1; or 15:1 and 50:1.

D. Additional Components

In some embodiments, the emulsion formulation includes an antioxidant. Examples of antioxidants include, but are not limited to, ascorbic acid, tocopherols, resveratrol, flavonoids, lycopene, carotenes L-cysteine, and carnosol. In some embodiments, ascorbic acid may be used in an emulsion formulation. In certain embodiments, the antioxidant is present at about 0.01 to about 10 mg/ml in the emulsion. In some embodiments, the emulsion contains about 0.1-1,1-2, 1-5, 1-10, or 5-10 mg/ml of antioxidant.

In another embodiment, the phospholipid is conjugated to an antibody or other targeting agent, enabling the directed delivery of the RNAi reagent into a specific target organ. The antibody recognizes tissue-specific targets, thereby concentrating delivery at those tissues. Other targeting agents include protein, carbohydrate, or small molecule ligands for tissue- or cell-specific receptors, viral vectors, and other targeting moieties known in the art.

II. PREPARATION METHODS

In some embodiments, the lipid component is prepared by mixing a neutral phospholipid and an oil with an organic solvent (e.g., chloroform, hexane). The organic solvent is removed from the resulting mixture using standard drying or evaporation methods known in the art. In some embodiments, the lipid component is frozen at −80° C. prior to drying or evaporation steps. The mixture may be frozen for at least 10, 20, or 30 minutes prior to drying or evaporation. In certain embodiments, the drying or evaporation includes lyophilization or rotary evaporation. The resulting material may also be dried by passing a stream of an inert gas (e.g., nitrogen) over it.

In some embodiments, the non-ionic surfactant is added to the lipid mixture and dried with the lipids. The surfactant may also be added to the aqueous component before forming the emulsion, or it may be added to the lipid-aqueous mixture. In some embodiments, the aqueous component contains between about 0.1 to 20 mg/ml of RNAi, anti-miRNA, or aptamer agent. In certain embodiments, at least 5 µl of lipid component is used for formulating 100 µg of RNAi, anti-miRNA, or aptamer agent. In other embodiments, the volume of the lipid-aqueous emulsion is between about 1 µl and 1 ml.

In certain embodiments, the lipid component is combined with the RNAi, anti-miRNA, or aptamer agent in aqueous solution and mixed to form an emulsion. The emulsion may be produced by high energy mixing of the phospholipid, oil, surfactant and nucleic acid in aqueous solution. Suitable high energy methods for mixing include sonication, extrusion, homogenization, pressurization, heating, freezing, crushing, laser light exposure, stirring, treating with other energetic motions or other methods known to those skilled in the art. In some embodiments, sonication is performed for at least 5, 10, 15, 20, 25, or 30 minutes. In other embodiments using extrusion, the pore size of the extrusion membrane may be less than 50 nm, 100 nm, 150 nm, 200 nm, or 400 nm. Emulsions may be further processed by separating out particles by size, for example by size, density, or field flow fractionation or chromatography.

The emulsion formulations may comprise liposomes, which are lipid containing vesicles having a lipid bilayer, as well as other lipid carrier particles that can entrap nucleic acid agents. The liposomes can be made of neutral phospholipids. Suitable phospholipids include DOPC, DOPE and others listed herein. The liposomes may be unilamellar, multilamellar or have an undefined lamellar structure. In some aspects, the liposomes entrap, encapsulate and/or incorporate the nucleic acid agent, such that the agent is enclosed or associated with some portion of the liposomes. In some embodiments, the lipid particles form micelles. Micelles may have an oil core surrounded by neutral phospholipid. In other embodiments, the lipid particles may exist as reverse micelles. The nucleic acid may be contained within the lipid particles, on the surface, and/or in the aqueous phase of the emulsion.

In certain embodiments, the lipid component and the aqueous component are combined in a ratio of about 1:1 to about 1:1000 by weight. The ratio of the lipid component and the aqueous component can be about 1:1, 1:5, 1:50, 1:100, 1:500 or 1:1000. Ranges of ratios are also encompassed within this range, such as the various sub-ranges that comprise the ratios included and between the listed values. The overall concentration of nucleic acid in the emulsion formulation may be from about 0.1 μg/ml to about 10 mg/ml. In some embodiments, the nucleic acid concentration is from about 0.1-1, 0.1-2, 0.5-1, 1-2, 1-5, or 1-10 mg/ml.

In some embodiments, at least 50, 60, 70, 80, or 90% of the nucleic acid is associated with the lipid particles. The formulations may be characterized using methods known in the art.

III. USE OF EMULSION FORMULATIONS

The emulsion formulations are used in many applications, including therapeutic and research purposes. The formulations are suitable for use in vertebrate animals such as cows, horses, pigs, monkeys, rabbits, rats, mice and humans. In other embodiments, this formulation may be used for delivering RNAi, anti-miRNA, or aptamer agents to other animals such as fish, frogs, shrimp, animals and plants used as food or for feed purposes, bugs including but not limited to ants, bees, flies, mosquitoes, gnats, crawling bugs, flying bugs, worms, or burrowing bugs. In other embodiments, the formulations can be applied to grass, farm plants, wild plants and trees.

Diseases and pathological conditions include, but are not limited to, proliferative, inflammatory, immune, metabolic, infectious, and ischemic diseases. Diseases also include neural, immune system, muscular, reproductive, gastrointestinal, pulmonary, cardiovascular, renal, proliferative, and/or cancerous diseases, disorders, and conditions. One of skill in the art will appreciate that silencing or reducing expression of genes associated with a disease or disorder can be combined with other conventional treatments.

Exemplary cancers include hematologic malignancies, leukemia (including acute leukemias (for example, acute lymphocytic leukemia, acute myelocytic leukemia, including myeloblastic, promyelocytic, myelomonocytic, monocytic, and erythroleukemia)) and chronic leukemias (for example, chronic myelocytic (granulocytic) leukemia and chronic lymphocytic leukemia), myelodysplastic syndrome polycythemia vera, lymphomas (for example, Hodgkin's disease and non-Hodgkin's disease), multiple myeloma, Waldenström's macroglobulinemia, heavy chain diseases, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, glandular carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, thyroid carcinoma or sarcoma, lung carcinoma, non-small cell lung carcinoma, small cell lung carcinoma, bladder cancer, skin cancer (including, e.g., epithelial carcinoma, sarcoma, and melanoma), glioma, astrocytoma, medulloblastoma, craniopharyngioma, ependymoma, pinealoma, hemangioblastoma, acoustic neuroma, oligodendroglioma, menangioma, melanoma, neuroblastoma, retinoblastoma; and/or cancer metastases, including metastases in bone, liver, and lung.

The final material may be delivered or used according to any method known to those skilled in the art of drug applications including, but not limited to, the circulatory system, skin, eye, ears, nose, throat, anus, vagina and urethra. Possible methods for administration include intravenously (IV), subcutaneously (sub-Q), low pressure tail vein injection (LPTV), high pressure tail vein injection (HPTV), ingestion, intraperitoneally (IP), inhalation, intranasally, intrathecally, intertumorally, skin application, intramuscularly, intraocularly, or intracochlearly or a combination thereof. The PORE formulation can be delivered systemically, or locally to a specific tissue or tumor, for example. One of skill in the art will recognize which administration methods are appropriate depending on the disease being treated or the type of agent being administered.

In one embodiment, a composition for use as an emulsion formulation may be packaged in a kit. For example, a composition including a neutral phospholipid, an oil, and a non-ionic surfactant may be packaged in a vial. In some embodiments, the composition contains a neutral phospholipid and an oil in a first vial, and a non-ionic surfactant in a second vial. The kit may include the RNAi, anti-miRNA, or aptamer agent in a dried form, wherein the agent is acceptable for the injection and is RNase free. In an alternate embodiment, the surfactant may be mixed with the nucleic acid agent. The kit may also include a buffer composition capable of reconstituting the dried form of the RNAi agent. The kit may also include a delivery device (e.g., a syringe) for delivery of the therapeutic agent after mixing with the composition.

IV. EXAMPLES

The following examples illustrate various embodiments of the invention and are not intended to limit the scope of the invention.

Example 1

The Making of and Microscopic Examination of a Phospholipid-Oil-RNAi Emulsion (PORE)

siRNA and miRNA reagents were purchased from Qiagen, Sigma, IDT or Applied Biosystems. Phospholipids were acquired from Sigma chemical or Avanti lipids. Squalene was purchased from Sigma.

A composition of 100 μg ascorbic acid, 3 μl of squalene (the oil), 1 mg 2-dioleoyl-sn-glycerol-3-phosphocholine (DOPC) (the neutral phospholipid), 49 μl of Tween 20 and 1 ml of chloroform was mixed in a 10 ml glass vial containing a solvent resistant screw cap by vortexing for 30 seconds. The molar ratio of squalene to DOPC was about 200:1. The mixture was incubated at −80° C. for at least 10 minutes. The chloroform was lyophilized using a rotary evaporator at 40° C., and the mixture was returned to −80° C. for at least 20 minutes. The lyophilized composition was dried further by passing a stream of nitrogen gas over it using direct nitrogen blowing using a steady stream. The resulting composition is very viscous, like heavy oil, and was centrifuged at 5,000 rpm using a TJ-6 centrifuge (Beckman; Fullerton, Calif., USA) so that the reagent accumulated at the bottom of the vial.

A 100 μg sample of miRNA dissolved in 150 μl of PBS was added directly to the lyophilized phospholipid-oil mixture and sonicated at room temperature for 10 minutes at 80 KHz and 80 watts using a G112SP1 Ultrasonic Cleaner (Laboratory Supplies Company, New York, USA). The molar ratio of squalene to miRNA was about 1:1. The temperature of the water in the Ultrasonic Cleaner was controlled. If the temperature rose above 40° C., then ice was added to the water to lower the temperature. The resulting material is a phospholipid-oil-RNAi emulsion (PORE).

The PORE was microscopically analyzed at 100× magnification. In many cases, large structures were found to be present in the solution. These large lipid/oil structures contained liposomes within them. The structures appear to be a mixture of large oil droplets (100 to 1000 μm) in some cases surrounding a number of smaller liposomes (0.1 to 10 μm). The RNAi agents are likely entrapped and encapsulated by more than one vesicle (vesicles inside vesicles). This unique mixture of agents might protect the RNAi agents from nucleases within the body and endow greater circulatory life.

Example 2

GAPDH Reduction in Mice Using siRNA Formulated with Neutral Phospholipid

Figure 4:
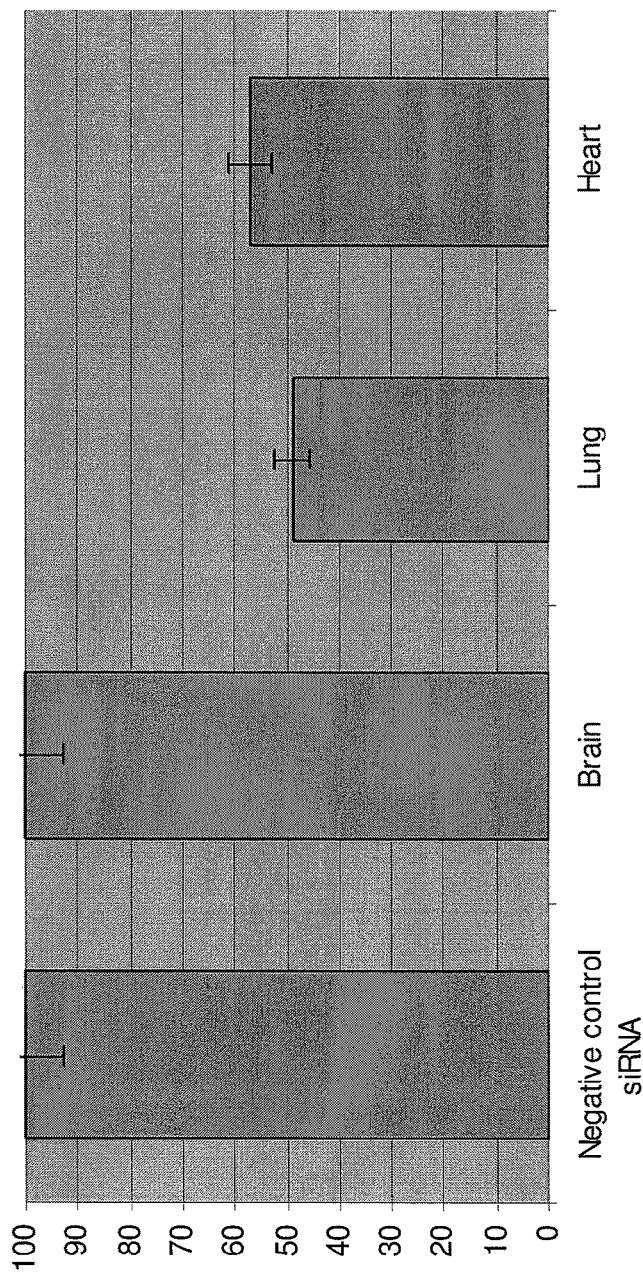
FIG. 4 indicates the relative GAPDH protein levels in the organs of mice injected with PORE containing GAPDH siRNA. The relative levels of GAPDH are compared to mice treated with a negative control siRNA.

A solution of 100 μg of GAPDH siRNA in 200 μp of PBS was added to a lyophilized phospholipid-oil mixture of 100 μg ascorbic acid, 3 μl squalene, 1 mg DOPC and 49 μl Tween 20, prepared by the method of Example 1. The mixture was sonicated for 5 minutes using 80 KHz and 80 watts using an 112SP1 Special Ultrasonic Cleaner (Laboratory Supplies Company, New York) to produce the PORE. The PORE was injected into the tail vein of mice. Seventy-two hours post injection, the animals were sacrificed, the organs removed, protein extracted using the protein extraction buffer supplied in the GAPDH ELISA kit (Bioo Scientific, CAT#3401) and normalized using a Bradford assay (Bioo Scientific, Catalog #: 3440-01). GAPDH concentrations were assayed using a GAPDH ELISA (Bioo Scientific, CAT#3401). Protein reduction is represented relative to a negative control RNAi agent treated animal (Qiagen negative control siRNA, CAT #S104381048). GAPDH activity was reduced by two-fold in the heart and lung (FIG. 4).

Example 3

Figure 5:
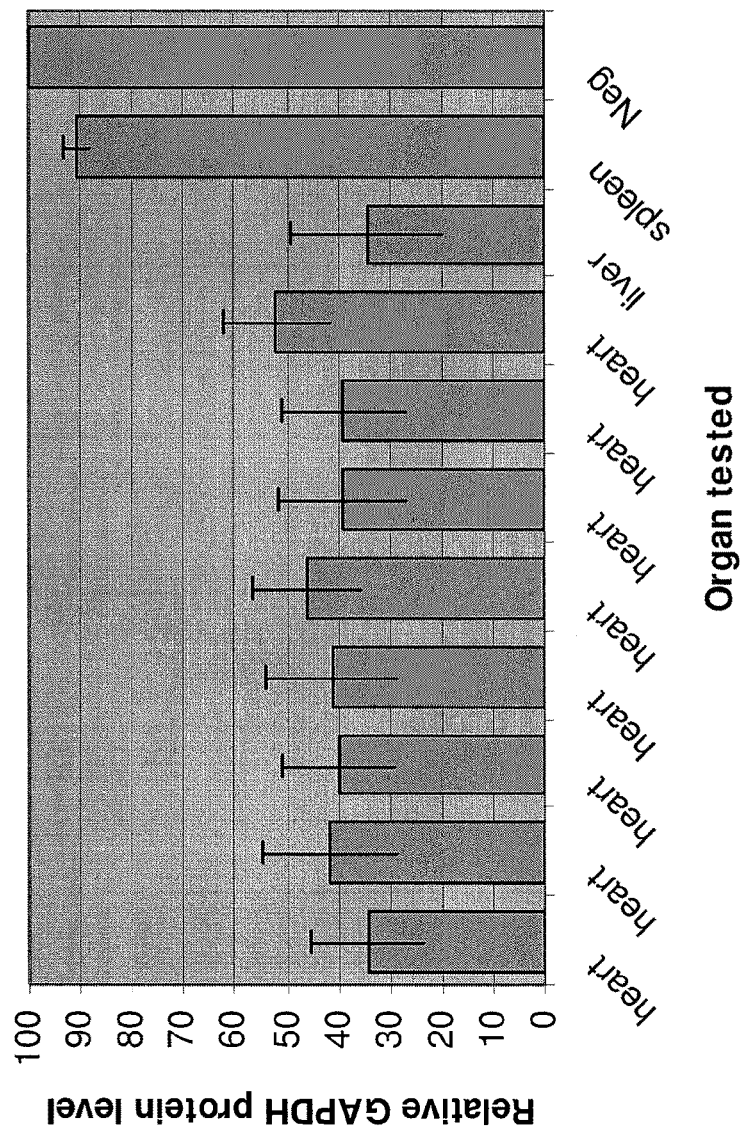
FIG. 5 indicates the relative GAPDH protein levels in the organs of rats injected with PORE containing GAPDH siRNA. The relative levels of GAPDH are compared to rats treated with a negative control siRNA.

GAPDH Reduction in Rat Heart Using siRNA Formulated with Neutral and Cationic Phospholipid A formulation containing squalene, DOTAP (cationic phospholipid), 0.8 DOPE (neutral phopspholipid) was mixed with GAPDH siRNA (Qiagen GAPDH positive control, Cat. #GS14433). A mixture of 12.5 μl of squalene, 3.2 mg of DOTAP, 0.8 mg of DOPE was dissolved in 1 ml chloroform. The mixture was incubated at −80° C. for at least 10 minutes. The chloroform was lyophilized using a rotary evaporator at 40° C., and the mixture was returned to −80° C. for at least 20 minutes, then dried using a dry nitrogen stream. A solution of 400 μg of GAPDH siRNA (Qiagen, Cat. #GS14433) in 200 μl of PBS was added directly to the phospholipid-oil mix and sonicated for five minutes using 80 KHz and 80 watts using an 112SP1 ultrasonic cleaner (The Laboratory Supplies Company, New York). Each out-bred rat (Jackson Labs; Bar Harbor, Me., USA) was injected in the tail vein with 400 μg of formulated siRNA. Seventy-two hours post injection the animals were sacrificed using gaseous carbon dioxide, the hearts were removed and cut into 8 equal pieces. Single pieces of the liver and spleen were also removed. Protein was extracted from tissues using the GAPDH ELISA kit protein extraction buffer (Bioo Scientific, cat. #3401). Protein was normalized using the Bradford assay (Bioo Scientific, cat. #3440-01). GAPDH concentration was assayed using a GAPDH ELISA (Bioo Scientific, cat. #3401). GAPDH concentrations were reduced by 50-60% in each piece in the test animals (FIG. 5). For rats, the total volume of the injected material did not exceed 0.5 ml of solution into the tail vein.

Example 4

GAPDH Protein Reduction in Mouse Heart

Figure 6:
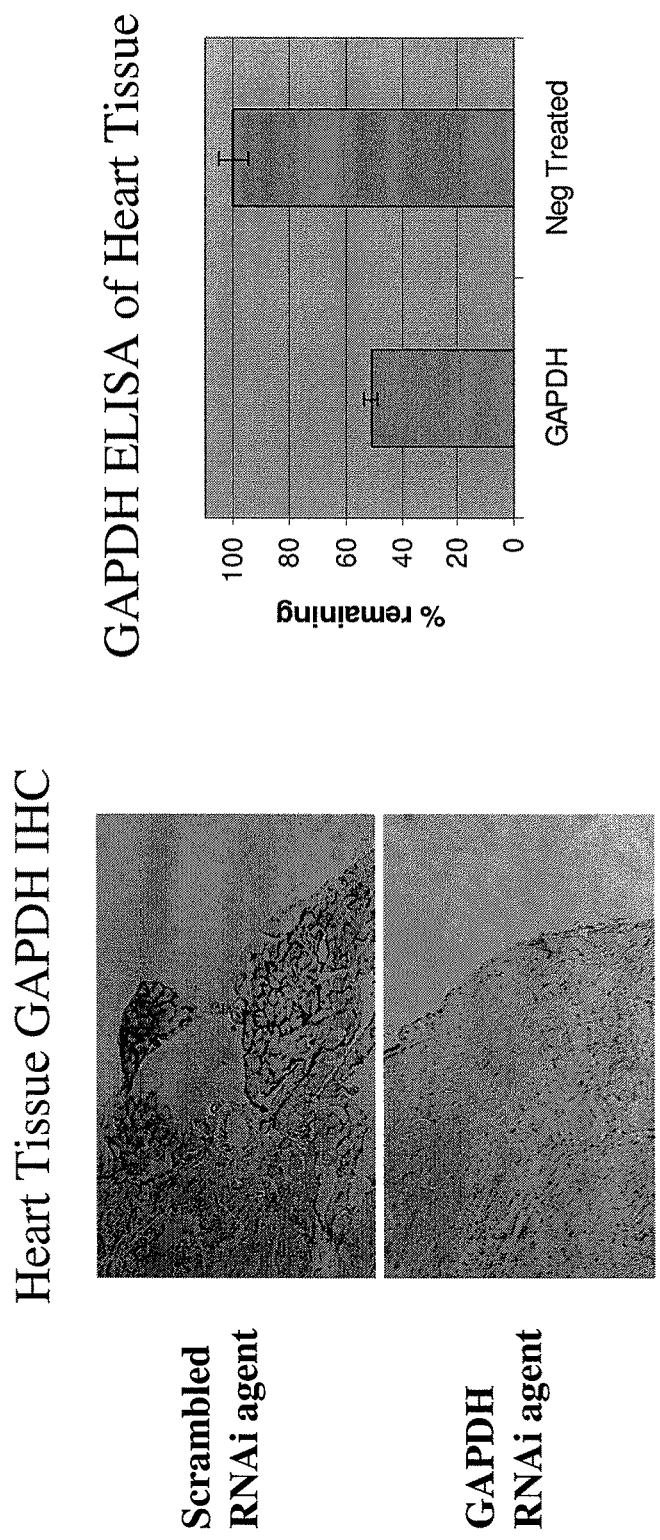
FIG. 6 indicates the relative GAPDH protein levels as assessed by immunohistochemistry and by ELISA in the mouse heart after mice have been injected with PORE containing GAPDH siRNA. The relative levels of GAPDH are compared to mice treated with a negative control siRNA.

A 1 ml volume of chloroform was mixed with 100 μg ascorbic acid, 3 μl squalene, 1 mg DOPC and 49 μl of Tween 20. The mixture was incubated at −80° C. for at least 10 minutes. The chloroform was lyophilized using a rotary evaporator at 40° C., and the mixture was returned to −80° C. for at least 20 minutes, then dried using a dry nitrogen stream. A 100 μg solution of GAPDH siRNA (Qiagen, Cat. #GS14433) in 100 μl PBS was added directly to the lyophilized material and sonicated for 5 minutes. The GAPDH PORE was injected into the tail vein of balb/c mice, 100 μg per mouse. Seventy-two hours post injection the animals were sacrificed. The hearts were removed and either embedded in paraffin for analysis of GAPDH protein by immunohistochemistry (the service provider from the Lester and Sue Smith Breast Center at Baylor College of Medicine, Houston Tex.) or protein was extracted from tissues using the GAPDH ELISA kit protein extraction buffer. The extracted protein was normalized using a Bradford assay (Bioo Scientific, cat. #3440-01). The GAPDH protein levels were then quantified using the Bioo GAPDH ELISA kit (Bioo Scientific, cat. #3401). GAPDH levels in the test animals were reduced 50% in the test animals (FIG. 6). The immunohistochemistry results corroborated the ELISA results indicating a reduction in GAPDH protein in the test animals based on the intensity levels of the GAPDH protein (brown).

Example 5

Efficacy of the PORE Formulated RSV siRNA Against a Viral Challenge

A 1 ml volume of chloroform was mixed with 100 μg ascorbic acid, 3 μl squalene, 1 mg DOPC and 49 μl of Tween 20. The mixture was incubated at −80° C. for at least 10 minutes. The chloroform was lyophilized using a rotary evaporator at 40° C., and the mixture was returned to −80° C. for at least 20 minutes, then dried using a dry nitrogen stream. A 100 μg solution of Respiratory Syncytial Virus (RSV) siRNA in 100 μl PBS was added directly to the lyophilized material and sonicated for 5 minutes. The RSV siRNA was also formulated with TransIT-TKO® Transfection Reagent (Mirus Bio Corporation, Madison, Wis.) and with Infasurf® (Forest Pharmaceuticals, Inc) as described (Bitko et al, 2005).

Figure 7:
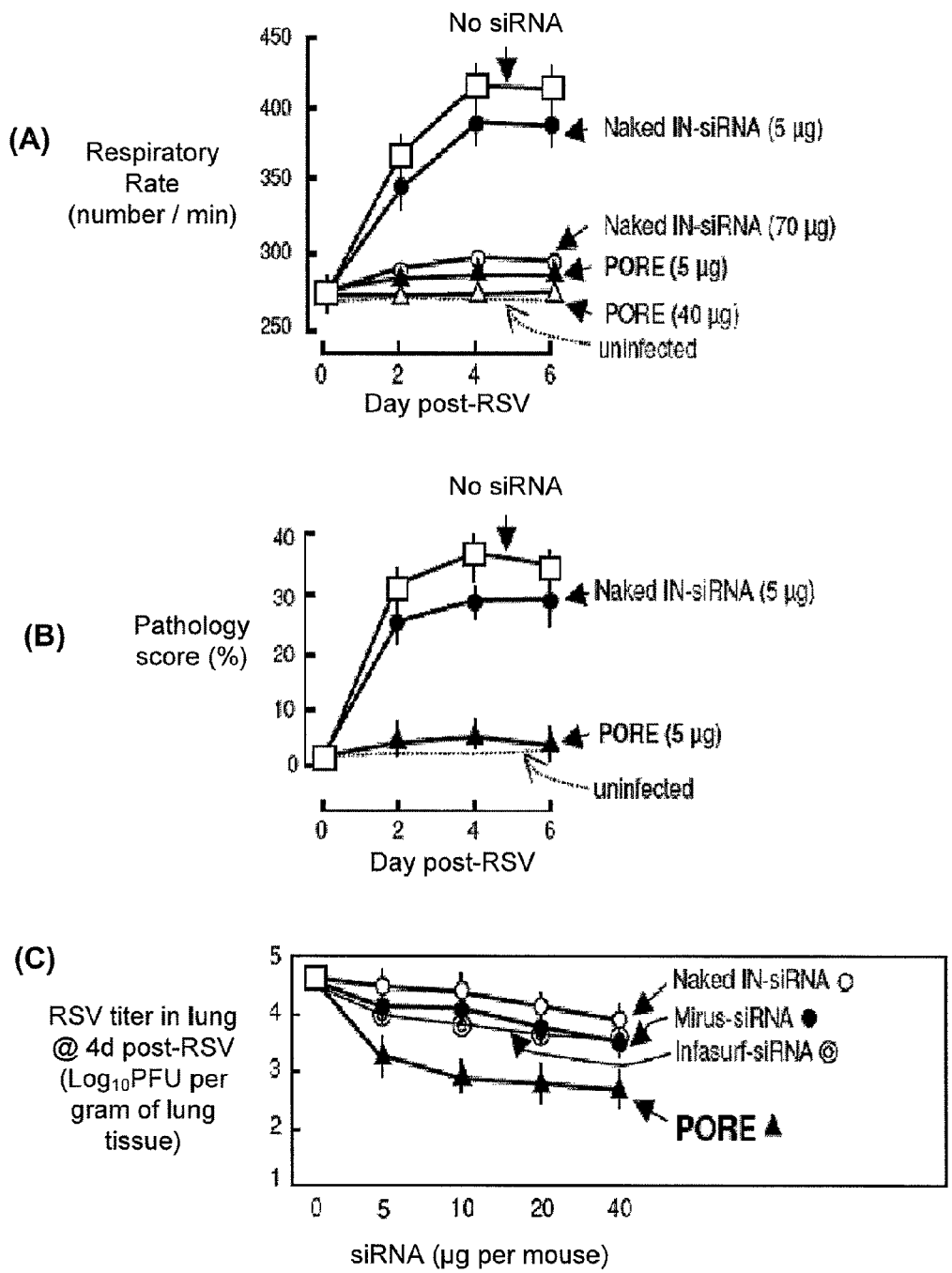
FIG. 7A reflects the respiratory rates of uninfected mice or respiratory syncytial virus (RSV) infected mice treated with a PORE-formulated RSV siRNA, without any formulation (naked siRNA) or without any siRNA treatment.
FIG. 7B indicates the pathology scores of mice treated with PORE-formulated RSV siRNA, without any formulation (naked siRNA) or without any siRNA treatment.
FIG. 7C is a graph indicating the RSV titers, 4 days post-challenge, of the mice treated with PORE-formulated RSV siRNA, Infasurf®, TransIT-TKO®, or no formulation (naked siRNA).

The three different RSV siRNA formulations and a non-formulated siRNA in PBS were administered to the mice intranasally with different doses of siRNA in replicates of three to assess the efficacy of each formulation. Mice were infected with $1 \times 10^7$ RSV as described (Bitko et al, 2005) 4 h after the siRNA administration. The effects of RSV infection were monitored at 0, 2, 4 and 6 days post challenge by three different criteria: respiratory rate, an H & E stained lung pathology score and RSV titer (FIG. 7).

Mice treated with the 5 μg RSV PORE had respiratory rates similar to the uninfected mice whereas the mice treated with 5 μg of unformulated RSV siRNA had much higher respiratory rates, comparable to the infected mice without any treatment (FIG. 7A). About 70 μg of non-formulated siRNA was required to lower the respiratory rate to levels of uninfected mice. Hence, the RSV PORE was about 14× more potent than the unformulated RSV siRNA or the TransIT-TKO formulated RSV siRNA (data not shown).

Mice treated with the 5 μg RSV PORE had pathology scores similar to uninfected (normal) mice whereas the infected mice treated with 5 μg of non-formulated RSV siRNA had pathology scores similar to the infected, untreated mice (FIG. 7B).

RSV infected mice, 4 days post challenge (when the viral concentrations are projected to reach a maximum), treated with RSV PORE had RSV titers in the lung about 100-fold less than untreated, infected mice at all siRNA concentrations (FIG. 7C). Even 40 μg of the other three RNA siRNA formulations caused no more than about a 10-fold reduction compared to the untreated, infected mice.

Example 6

Comparison of PORE and DOPC Formulations

Figure 8:
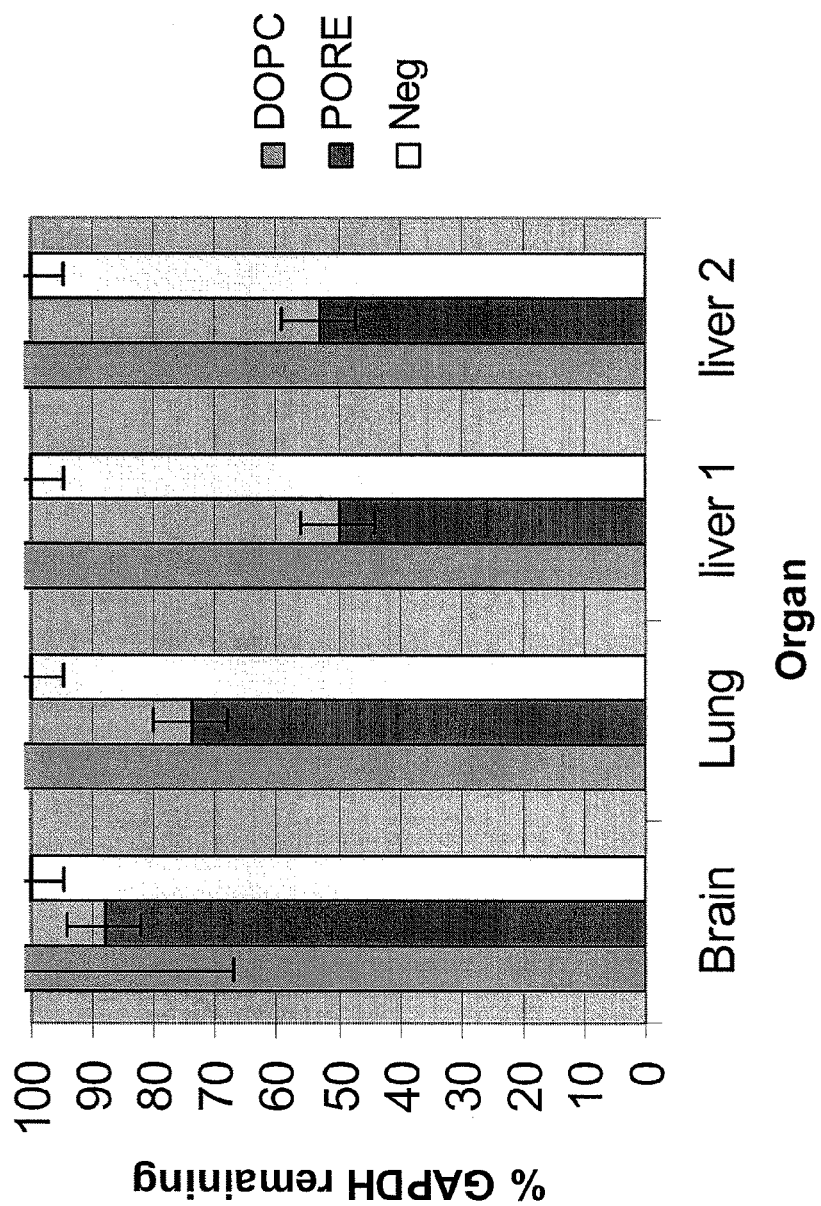
FIG. 8 is a graph demonstrating the improvement of gene reduction obtained by adding squalene into a formulation containing a neutral lipid.

A 1 ml volume of chloroform was mixed with either 100 μg ascorbic acid, 3 μl squalene, 1 mg DOPC and 49 μl of Tween 20 (PORE formulation) or 1 mg DOPC and 49 μl of Tween 20 (DOPC). The mixtures were incubated at −80° C. for at least 10 minutes. The chloroform was lyophilized using a rotary evaporator at 40° C., and the mixtures were returned to −80° C. for at least 20 minutes, then dried using a dry nitrogen stream. A 100 μg solution of GAPDH siRNA (Qiagen, Cat. #GS14433) in 100 μl PBS was added directly to the lyophilized material and sonicated for 5 minutes. The GAPDH PORE or DOPC formulation was injected into the tail vein of balb/c mice, 100 μg per mouse. Seventy-two hours post injection the animals were sacrificed. Next, protein was extracted from tissues using the GAPDH ELISA kit protein extraction buffer (Bioo Scientific, cat. #3401). Protein was normalized using the Bradford assay (Bioo Scientific, cat. #3440-01). GAPDH concentration was assayed using a GAPDH ELISA (Bioo Scientific, cat. #3401). GAPDH concentrations were reduced by 50-60% in the livers of mice treated with PORE formulated siRNA but not with DOPC formulated siRNA (FIG. 8).

Example 7

Effects of Various Oils/Waxes and Neutral Lipids to Delivery siRNAs to Normal Tissues To assess the ability of various oils/waxes and neutral lipids to deliver an siRNA to various tissues following IV injection, the PORE formulations listed in Table 1 are prepared with an siRNA targeting GAPDH or a negative control siRNA using the standard protocol (see Example 1). The various formulations+siRNAs are introduced to BalbC mice via tail vein injection at a rate of 5 mg/kg. Two days after injection, the mice are sacrificed and brain, liver, heart, spleen, left kidney, right kidney, left lung, and right lung are removed. Protein preparations from the various tissues are subjected to Bradford analysis and then samples with equal mass amounts of protein are subjected to ELISA to quantify the GAPDH protein.

TABLE 1

Compositions of DOPC-based oil emulsions using various oils and waxes.

| Components | variant 1 | variant 2 | variant 3 | variant 4 | variant 5 |
|---|---|---|---|---|---|
| Ascorbic acid 10 mg/ml | 10 ul | 10 ul | 10 ul | 10 ul | 10 ul |
| Squalene: 100% | 0 ul | 3 ul | N/A | N/A | N/A |
| DOPC: 20 mg/ml | 50 ul | 50 ul | 50 ul | 50 ul | 50 ul |
| Tween 20: 100% | 50 ul | 50 ul | 50 ul | 50 ul | 50 ul |
| Coconut oil | N/A | N/A | 3 ul | N/A | N/A |
| Steedmans wax | N/A | N/A | N/A | 3 ul | N/A |
| Palm oil | N/A | N/A | N/A | N/A | 3 ul |

Abbreviations:
N/A, not added

Example 8

Delivery of siRNA to Orthotopic Lung Tumor Xenografts in Mice

Previous examples indicated successful delivery and activity of small interfering RNA to various normal tissues, including lung. In this example, the inventors demonstrate the utility of the neutral phospholipid-based emulsion as a delivery vehicle for oligonucleotides in an orthotopic lung tumor mouse model. Human H460 non-small cell lung cancer xenografts stably expressing the firefly luciferase gene were grown in the lungs of mice (orthotopic mouse model for lung cancer), and a luciferase-directed siRNA (si-luc) was used to demonstrate systemic delivery by PORE to tumor cells. In this assay system, a reduction in luciferase activity would indicate (i) successful delivery of the luciferase-directed siRNA to the lung, (ii) successful delivery of siRNA to tumors cells grown in the lung, (iii) successful intracellular uptake of siRNA by tumor cells and (iv) successful entry of siRNA into the RNAi pathway and knock-down of its intended target. Therefore, the use of luciferase-expressing tumor cells and a luciferase-directed siRNA provides an accurate and sensitive assessment of delivery as well as activity of the oligonucleotide. This model system accounts for all physical barriers that a systemically-delivered oligonucleotide has to pass before it becomes therapeutically active.

A solution of 20 μg of synthetic luciferase-specific siRNA (si-luc; Ambion, Austin, Tex., USA) or a solution of 20 μg of negative control oligonucleotide (NC; Dharmacon, Lafayette, Colo.) in 200 μl of PBS was added to a lyophilized phospholipid-oil mixture of 20 μg ascorbic acid, 0.6 μl squalene, 0.2 mg DOPC and 9.8 μl Tween 20, prepared by the method of Example 1. The final concentration of the oligonucleotide in PORE was 100 ng/μl.

$3 \times 10^6$ H460 lung cancer cells were grafted into the lungs of 4 immunocompromised NOD/SCID mice (Jackson Laboratories; Bar Harbor, Me., USA) by intratracheal intubation. Mice were regularly monitored by an IVIS® imaging system (Xenogen, Caliper Life Sciences, Hopkinton, Mass., USA) measuring luminescence (luciferase activity) following an intraperitoneal injection of the luciferase substrate luciferin. Since H460 cells stably express luciferase, the luminescent signal directly correlates with viable tumor cells. Once mice developed readily detectable lung tumors, total luminescence data were recorded (total flux, 0 hours). Immediately after measuring luminescence, two mice received intravenous tail-vein injections of 20 µg si-luc in 200 µl PORE. Given an average mouse weight of 20 g, this dose equals 1 mg per kg mouse body weight. As a negative control, two mice received intravenous tail-vein injections of 20 µg NC in 200 µl PORE formulations. Forty-eight hours after injection of formulated oligonucleotide, luminescence was measured again and expressed as percent change relative to the total flux of each mouse at 0 hours (100%).

Figure 9A:
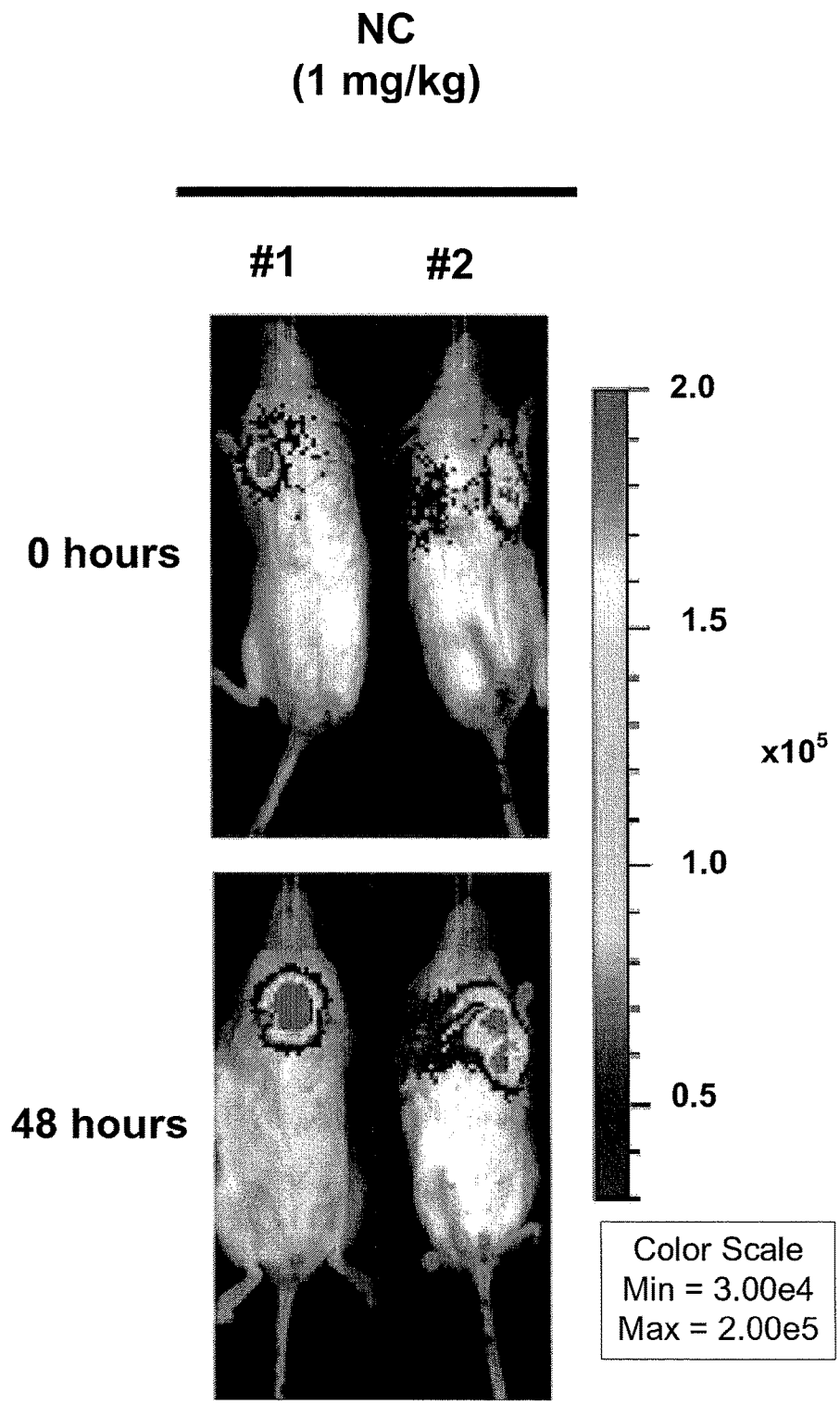
FIG. 9 shows results of systemic delivery of PORE-formulated luciferase-specific siRNA to orthotopic lung tumor xenografts in mice. Mice carrying human H460 non-small cell lung cancer tumor xenografts stably expressing luciferase and grown in the lungs received intravenous injections of PORE-formulated luciferase siRNA (si-luc) (FIG. 9B, animals #3 and #4) or PORE-formulated negative control oligonucleotide (NC) (FIG. 9A, animals #1 and #2) at a final concentration of 1 mg per kg mouse body weight (1 mg/kg). IVIS®) images showing the luminescent signal of active luciferase were taken just before injection of the formulations (0 hours) and 48 hours post-injection.
Figure 9B:
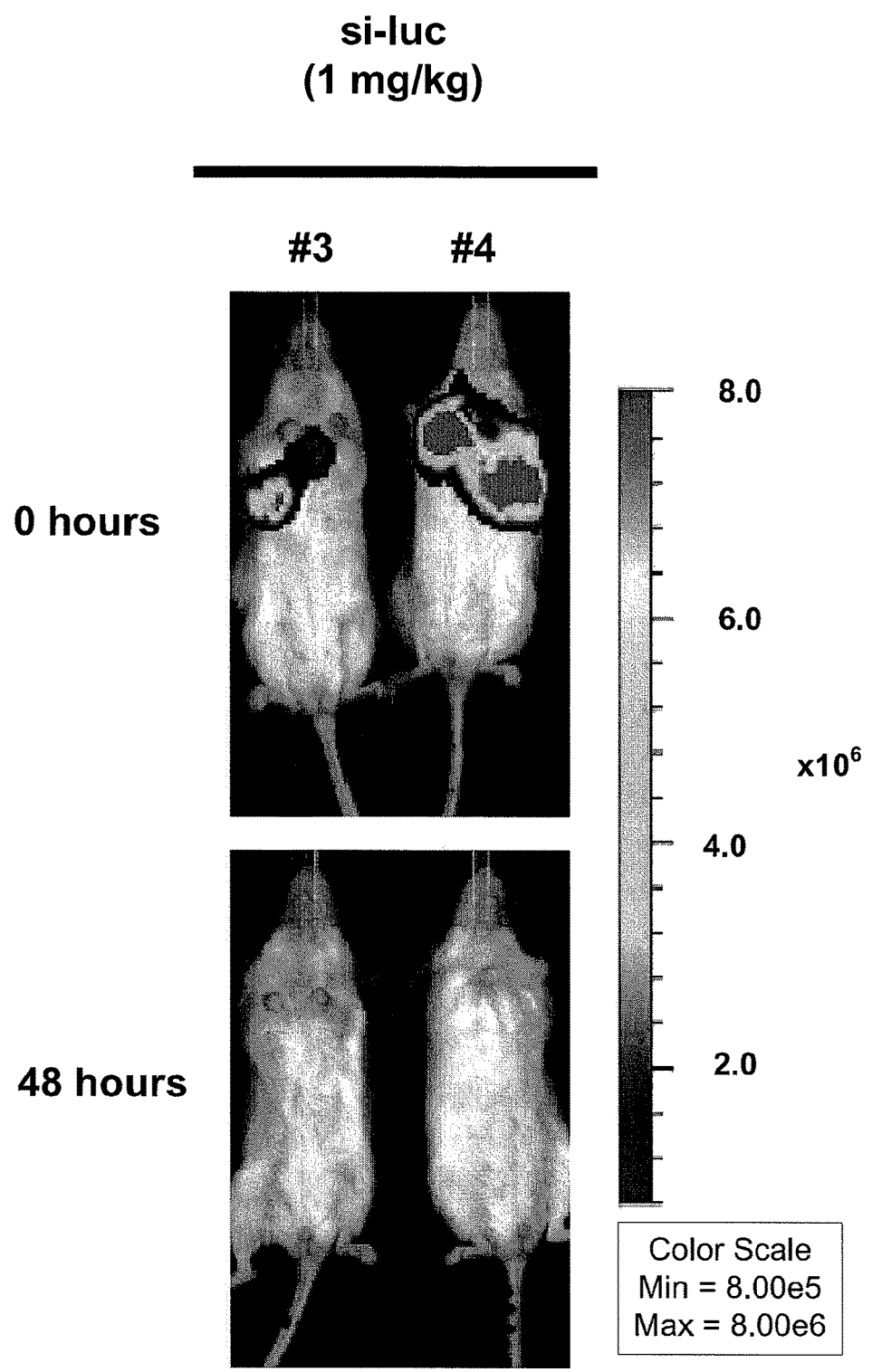
Figure 10:
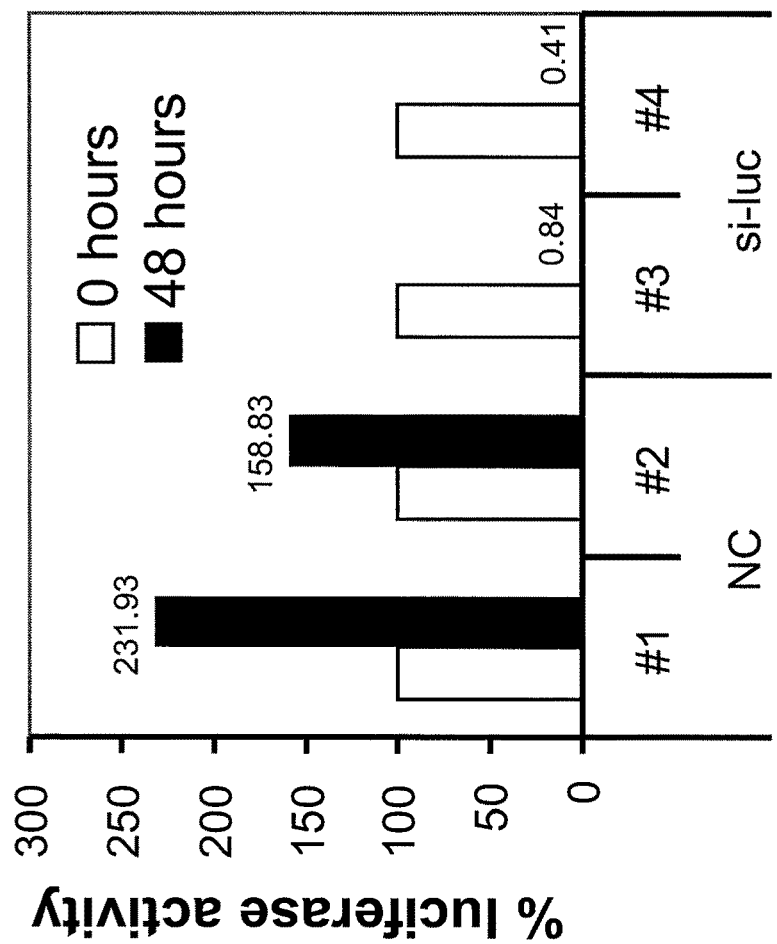
FIG. 10 displays luciferase activity in orthotopic lung tumors systemically treated with PORE-formulated luciferase siRNA. A quantification of IVIS® data from animals in FIG. 9 is shown. Total flux at 0 hours was set as 100% luciferase activity. The percent luciferase activity 48 hours post injection is shown in the graph.

As shown in FIG. 9A, systemic delivery of PORE containing NC had no inhibitory effect on the luciferase activity of H460 tumor cells (animals #1 and #2). In contrast, systemic administration of PORE-formulated si-luc led to a robust reduction in luciferase activity 48 hours post injection (FIG. 9B, animals #3 and #4). The remaining luciferase activity in animals treated with the luciferase siRNA was 0.84% and 0.41% relative to the ones at 0 hours, indicating that the luciferase siRNA was successfully delivered to tumor cells (FIG. 10).

The data illustrate that PORE facilitates efficacious delivery of luciferase siRNA to tumor cells.

Example 9

Intratumoral Delivery of Therapeutic miRNA in a PORE Formulation Inhibits Tumor Growth in Mice The therapeutic efficacy of hsa-miR-34a and hsa-miR-124a when complexed in the neutral phospholipid-based oil emulsion demonstrates the capacity of the neutral phospholipid based oil-emulsion to successfully deliver the therapeutic agent.

The inventors have previously demonstrated that hsa-miR-34a and hsa-miR-124a are involved in the regulation of numerous cell activities that represent intervention points for cancer therapy and for therapy of other diseases and disorders (see, e.g., U.S. application Ser. Nos. 11/141,707, 11/273,640, 12/134,932, and 12/325,917). For example, overexpression or administration of synthetic hsa-miR-34a or hsa-miR-124a decreases the proliferation and/or viability of certain normal or cancerous cell lines and interferes with tumor growth in the animal.

A solution of 100 µg of synthetic hsa-miR-34a, hsa-miR-124a or negative control miRNA oligo (miR-NC) (Dharmacon, Lafayette, Colo.) in 200 µl of PBS was added to a lyophilized phospholipid-oil mixture of 100 µg ascorbic acid, 3 µl squalene, 1 mg DOPC and 49 µl Tween 20, prepared by the method of Example 1 to reach a final concentration of the oligonucleotide in PORE of 500 ng/µl.

Each 3×10$^6$ human H460 non-small lung cancer cells were mixed with BD Matrigel™, (BD Biosciences; San Jose, Calif., USA; cat. no. 356237) in a 1:1 ratio and subcutaneously injected into the lower back of 28 NOD/SCID mice (Jackson Laboratories; Bar Harbor, Me., USA). Once animals developed palpable tumors (day 12 post xenograft implantation), groups of 7 animals received intratumoral injections of 100 µg hsa-miR-34a or hsa-miR-124a (Dharmacon, Lafayette, Colo.) formulated with PORE on days 12, 15 and 18 (injection volume=200 µl of 500 ng/µl oligo in PORE). A control group of 7 animals received intratumoral injections of each 100 µg negative control miRNA (miR-NC; Dharmacon, Lafayette, Colo.), following the same injection schedule that was used for hsa-miR-34a and hsa-miR-124a. In addition, a group of four H460 tumor-bearing mice received intratumoral injections of the phospholipid-oil emulsion without miRNA, and a group of 4 animals received intratumoral injections of phosphate-buffered saline (PBS). Caliper measurements were taken every 1-2 days, and tumor volumes were calculated using the formula, Volume=length×width×width/2, in which the length is greater than the width.

Figure 11:
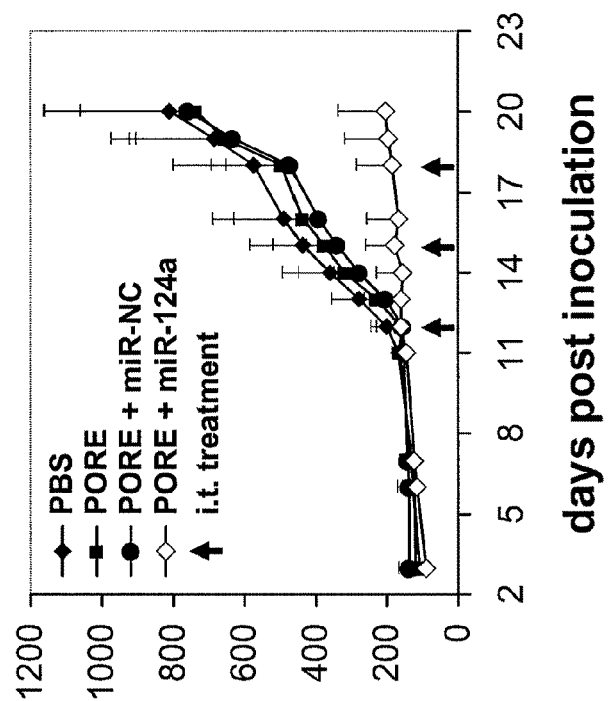
FIG. 11 shows intratumoral delivery of PORE-formulated therapeutic miRNAs. Palpable subcutaneous H460 non-small cell lung cancer xenografts were treated with a PORE containing hsa-miR-34a (FIG. 11A, white squares), hsa-miR-124a (FIG. 11B, white diamonds) or a negative control miRNA (FIGS. 11A and 11B, miR-NC, black circles). A separate set of tumor-bearing animals was treated with phosphate-buffered saline (PBS) or phospholipid-oil emulsion only (FIGS. 11A and 11B, black diamonds and black squares, respectively). Formulations were injected intratumorally (i.t.) on days 12, 15 and 18 post implantation of xenografts (arrows). Averages and standard deviations of 7 animals (miR-34a, miR-124, miR-NC) or 4 animals (PBS, phospholipid-oil only) are shown.
Figure 11:
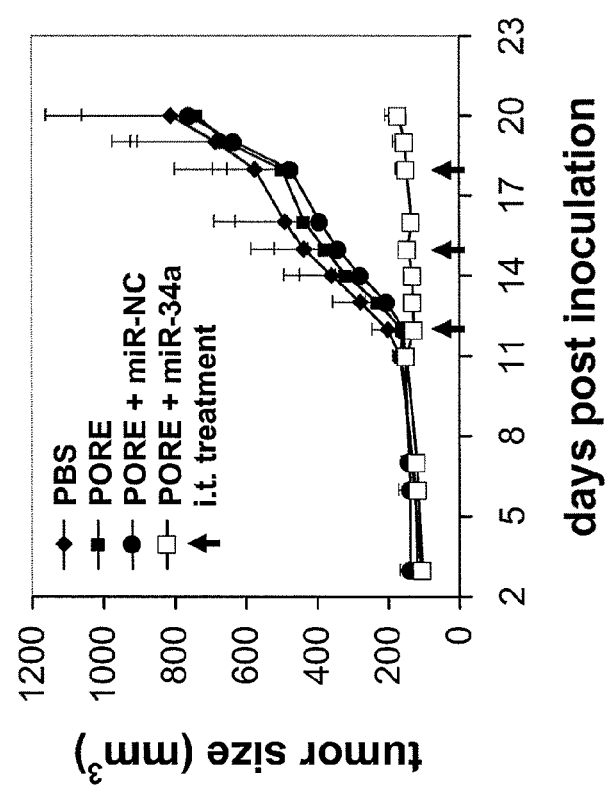

As shown in FIG. 11, three doses of formulated hsa-miR-34a (FIG. 11A, white squares) or three doses of PORE-formulated hsa-miR-124a (FIG. 11B, white diamonds) robustly inhibited growth of established H460 lung tumors. In contrast, tumors treated with PORE-formulated negative control miRNA (miR-NC, black circles) grew at a steady pace and yielded tumors with an average size that is comparable to tumors of animals treated with PBS or phospholipid-oil emulsion only (black diamonds and black squares). On day 20, the average volume of tumors treated with formulated hsa-miR-34a was 22.2% of tumors treated with formulated miR-NC with p values of <0.01 on days 13 through 20. Similarly, the average volume of tumors treated with formulated hsa-miR-124a on day 20 was 26.9% of tumors treated with formulated miR-NC, showing p values of <0.01 on days 14 through 20.

The data show that PORE facilitates successful delivery of the therapeutic miRNAs hsa-miR-34a and hsa-miR-124a into tumor cells which resulted in a robust and specific inhibition of tumor growth.

Example 10

Systemic Delivery of Therapeutic miRNA in a PORE Formulation Inhibits Tumor Growth in Mice The inventors assessed the capacity of neutral phospholipid-based oil emulsion to successfully deliver therapeutic oligonucleotides to tumor cells in vivo by systemic administration.

A solution of 100 µg of synthetic hsa-miR-34a, hsa-miR-124a or negative control miRNA oligo (miR-NC) (Dharmacon, Lafayette, Colo.) in 200 µl of PBS was added to a lyophilized phospholipid-oil mixture of 100 µg ascorbic acid, 3 µl squalene, 1 mg DOPC and 49 µl Tween 20, prepared by the method of Example 1 to reach a final concentration of the oligonucleotide in PORE of 500 ng/µl.

Each 3×10$^6$ human H460 non-small lung cancer cells were mixed with BD Matrigel™, (BD Biosciences; San Jose, Calif., USA; cat. no. 356237) in a 1:1 ratio and subcutaneously injected into the lower back of 16 NOD/SCID mice (Jackson Laboratories; Bar Harbor, Me., USA). After animals developed palpable tumors (day 12 post xenograft implantation), groups of 4 animals each received intravenous injections of 100 µg PORE-formulated hsa-miR-34a or hsa-miR-124a (Dharmacon, Lafayette, Colo.) on days 12, 15 and 18 (injection volume=200 µl of 500 ng/µl oligo in PORE). A control group of 4 animals each received intravenous injections of 100 µg PORE-formulated negative control miRNA (miR-NC; Dharmacon, Lafayette, Colo.), following the same injection schedule that was used for hsa-miR-34a and hsa-miR-124a. In addition, a group of four H460 tumor-bearing mice received intravenous injections of the phospholipid-oil emulsion without miRNA. Caliper measurements were taken every 1-2 days, and tumor volumes were calculated using the formula, Volume=length×width×width/2, in which the length is greater than the width.

Figure 12:
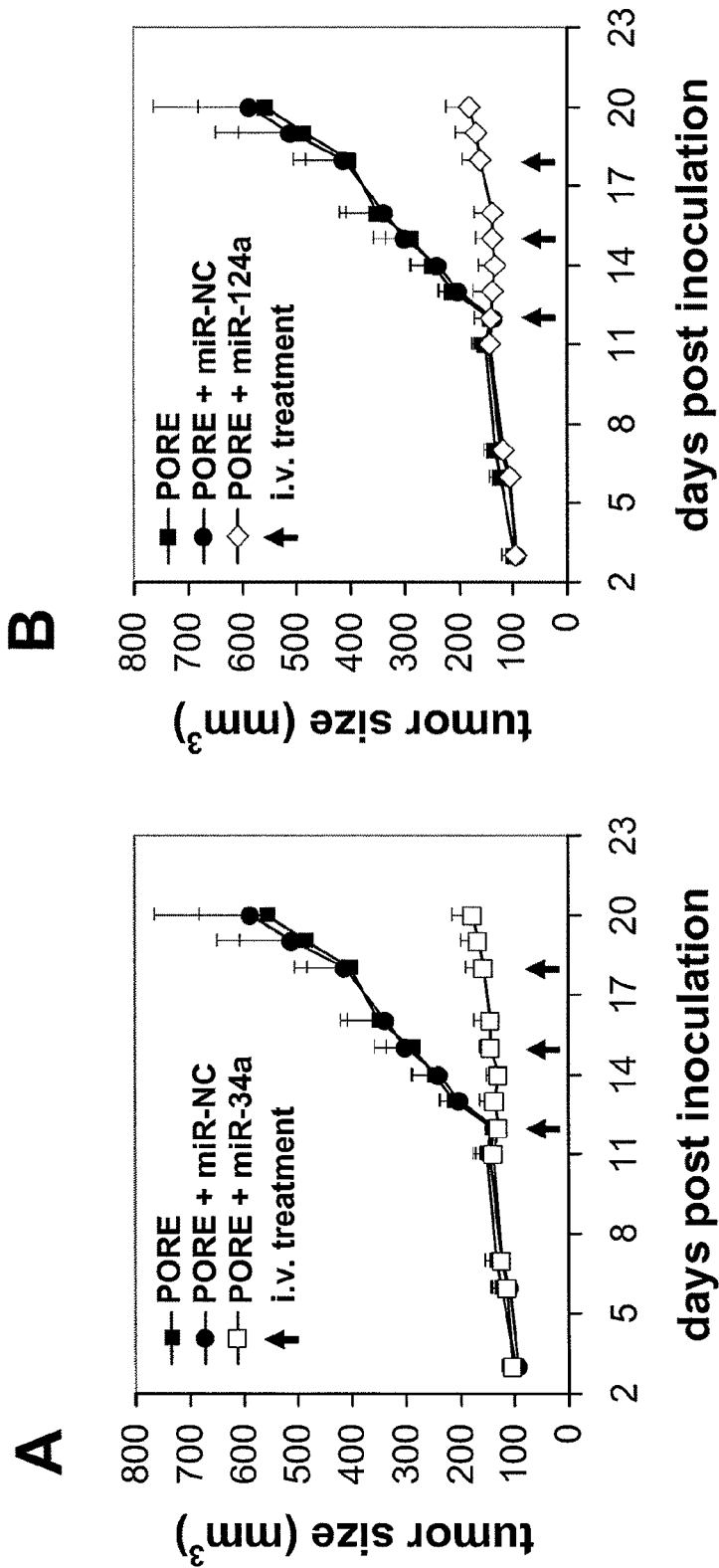
FIG. 12 shows results of systemic delivery of PORE-formulated therapeutic miRNAs. Mice carrying palpable subcutaneous H460 non-small cell lung cancer xenografts were treated systemically with a PORE containing hsa-miR-34a (FIG. 12A, white squares), hsa-miR-124a (FIG. 12B, white diamonds) or a negative control miRNA (FIGS. 12A and 12B, miR-NC, black circles). A separate set of tumor-bearing animals was treated with phospholipid-oil emulsion only (FIGS. 12A and 12B, black squares). Formulations were administered by tail vein injections (i.v.) on days 12, 15 and 18 post implantation of xenografts (arrows). Averages and standard deviations of 4 animals per group are shown.

As shown in FIG. 12, three doses of formulated hsa-miR-34a (FIG. 12A, white squares) or three doses of formulated hsa-miR-124a (FIG. 12B, white diamonds) robustly inhibited growth of established H460 lung tumors. In contrast, tumors treated with formulated negative control miRNA (miR-NC, black circles) grew at a steady pace and yielded tumors with an average size that is comparable to tumors of animals treated with phospholipid-oil emulsion only (black squares). On day 20, the average volume of tumors treated with formulated hsa-miR-34a was 30.1% of tumors treated with formulated miR-NC with p values of <0.01 on days 14 through 20. Similarly, the average volume of tumors treated with formulated hsa-miR-124a on day 20 was 30.8% of tumors treated with formulated miR-NC, showing p values of <0.01 on days 15 through 20.

The data show robust and specific inhibition of tumor growth.

Example 11

Systemic Delivery of Various Doses of Therapeutic miRNA in a PORE Formulation

The inventors evaluated the in vivo dose response of therapeutic oligonucleotides delivered systemically using neutral phospholipid oil emulsion formulations.

Synthetic hsa-miR-34a (Dharmacon, Lafayette, Colo.) was formulated with PORE following the experimental procedure described in Example 1. Various hsa-miR-34a formulations in PORE at 500 ng/µl, 100 ng/µl, 10 ng/µl and 1 ng/µl were prepared by adjusting the PORE ratio against the amount of total oligo, and adjusting for the desired concentration with phosphate-buffered saline (PBS). Given an injection volume of 200 µl, the following miRNA doses were used: 100 µg, 20 µg, 2 µg and 200 ng. Given an average mouse weight of 20 g, these doses represent 5 mg/kg, 1 mg/kg, 0.1 mg/kg and 0.01 mg/kg.

Each $3\times10^6$ human H460 non-small lung cancer cells were mixed with BD Matrigel™, (BD Biosciences; San Jose, Calif., USA; cat. no. 356237) in a 1:1 ratio and subcutaneously injected into the lower back of 15 NOD/SCID mice (Jackson Laboratories; Bar Harbor, Me., USA). Once animals developed palpable tumors (day 12 post xenograft implantation), groups of 3 animals received intravenous injections of each 200 µl PORE-formulated hsa-miR-34a at concentrations of 500 ng/µl, 100 ng/µl, 10 ng/µl and 1 ng/µl. As a negative control, a separate group of 3 tumor-bearing animals received each 200 µl PBS. Treatment was repeated on days 15 and 19. Caliper measurements were taken every 1-2 days, and tumor volumes were calculated using the formula, Volume=length×width×width/2, in which the length is greater than the width.

Figure 13A:
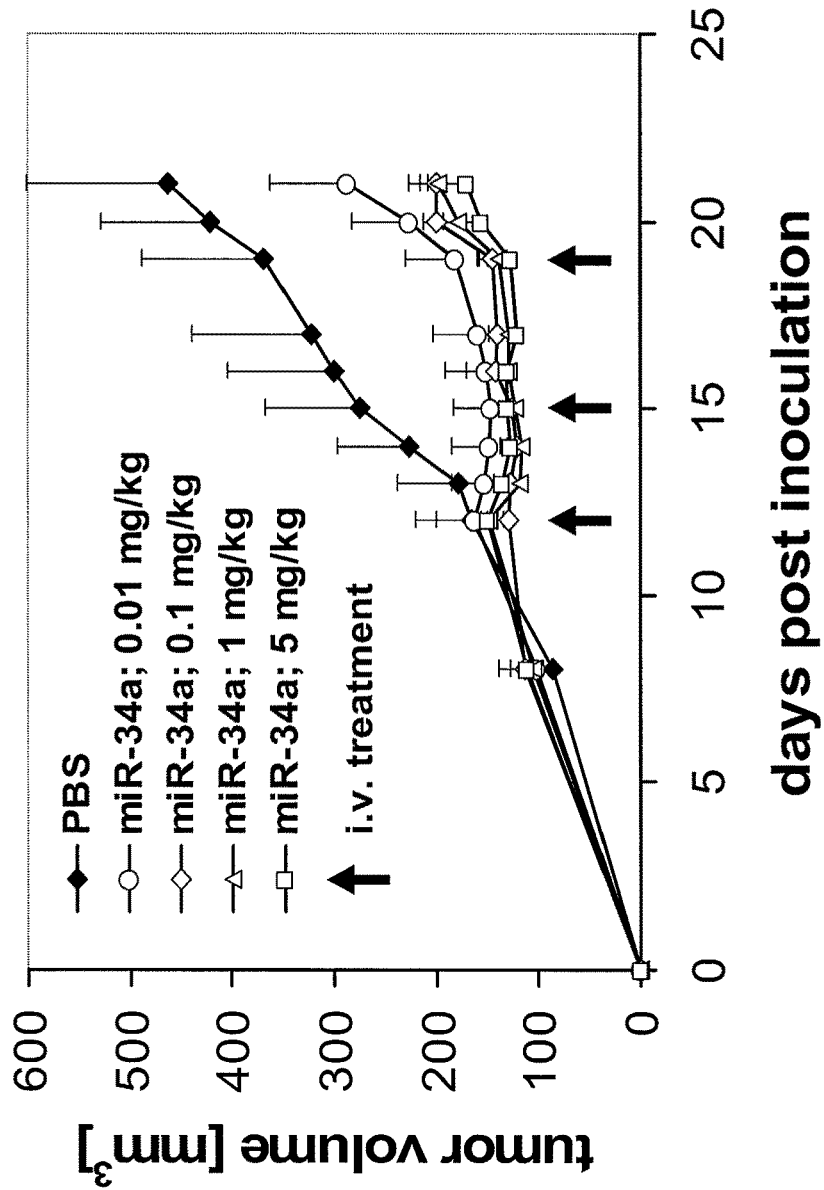
FIG. 13 shows results of systemic delivery of various doses of PORE-formulated therapeutic miRNA. Mice harboring established subcutaneous human H460 non-small cell lung cancer xenografts were intravenously injected with PORE-formulated hsa-miR-34a oligonucleotide. Doses used and days of treatment are shown in the graph. As a control, phosphate-buffered saline was injected into a separate group of tumor-bearing animals. Averages and standard deviations of 3 animals per group are shown. The data are plotted either as total tumor volumes (FIG. 13A) or percent tumor growth relative to day of first treatment (FIG. 13B, day 12,100%).
Figure 13B:
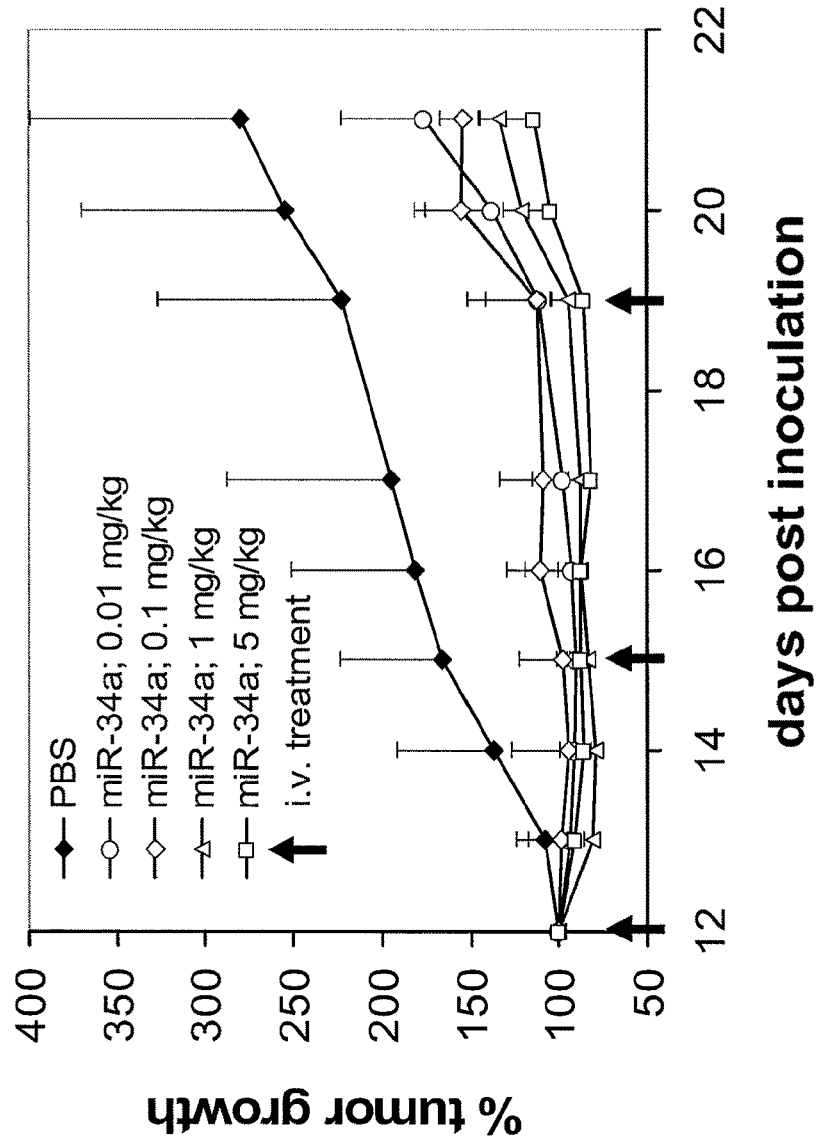

As shown in FIG. 13A, hsa-miR-34a inhibited tumor growth at all doses used relative to PBS. Maximal inhibition of tumor growth was achieved at the highest dose (5 mg/kg), and hsa-miR-34a at 0.01 mg/kg had the least therapeutic effect. P values of hsa-miR-34a data in a comparison to the PBS data ranged <0.05 (5 mg/kg, days 14, 15 and 20; 1 mg/kg, days 15-21; 0.1 mg/kg, days 19-21; 0.01 mg/kg, day 20) and <0.01 (5 mg/kg, days 16-19 and day 21), indicating statistical significance. To directly compare the effects of hsa-miR-34a at various doses, tumor volumes were plotted as percent change relative to their respective tumor volumes on day 12 (start of treatment, 100%; FIG. 13B). The dose-dependent effect of hsa-miR-34a is in agreement with the general kinetics of therapeutic agents, and indicates that inhibition of tumor growth is a specific response to the therapeutic.

Example 12

Delivery of Therapeutic miRNA to Orthotopic Lung Tumor Xenografts in Mice

In Example 8, the inventors illustrated the capacity of neutral phospholipid-based oil to deliver small oligonucleotides to orthotopically grown lung tumors in mice using a luciferase-directed siRNA. In this Example, PORE-formulated therapeutic miRNA oligonucleotides were used to inhibit orthotopically grown lung tumors in mice.

Synthetic hsa-miR-124a (Dharmacon, Lafayette, Colo.) was formulated with PORE at a final concentration of 100 ng/µl oligo as described in Example 1.

Each $3\times10^6$ H460 lung cancer cells were grafted into the lungs of immunocompromised NOD/SCID mice (Jackson Laboratories; Bar Harbor, Me., USA) by intratracheal intubation. Mice were regularly monitored by an IVIS® imaging system (Xenogen, Caliper Life Sciences, Hopkinton, Mass., USA) measuring luminescence (luciferase activity) following an intraperitoneal injection of the luciferase substrate luciferin. Since H460 cells stably express luciferase, the luminescent signal directly correlates with viable tumor cells. Once mice developed readily detectable lung tumors (day 39 post inoculation), one mouse received 200 µl intravenous tail-vein injections of 20 µg PORE-formulated hsa-miR-124a. Given an average mouse weight of 20 g, this dose equals 1 mg per kg mouse body weight. As a control, a mouse carrying a lung tumor with similar size was used and left untreated throughout the entire experiment. Intravenous injections with PORE-formulated hsa-miR-124a were repeated every other day for the following 13 days. Luminescence was recorded frequently, and both mice were sacrificed on day 52.

Figure 14A:
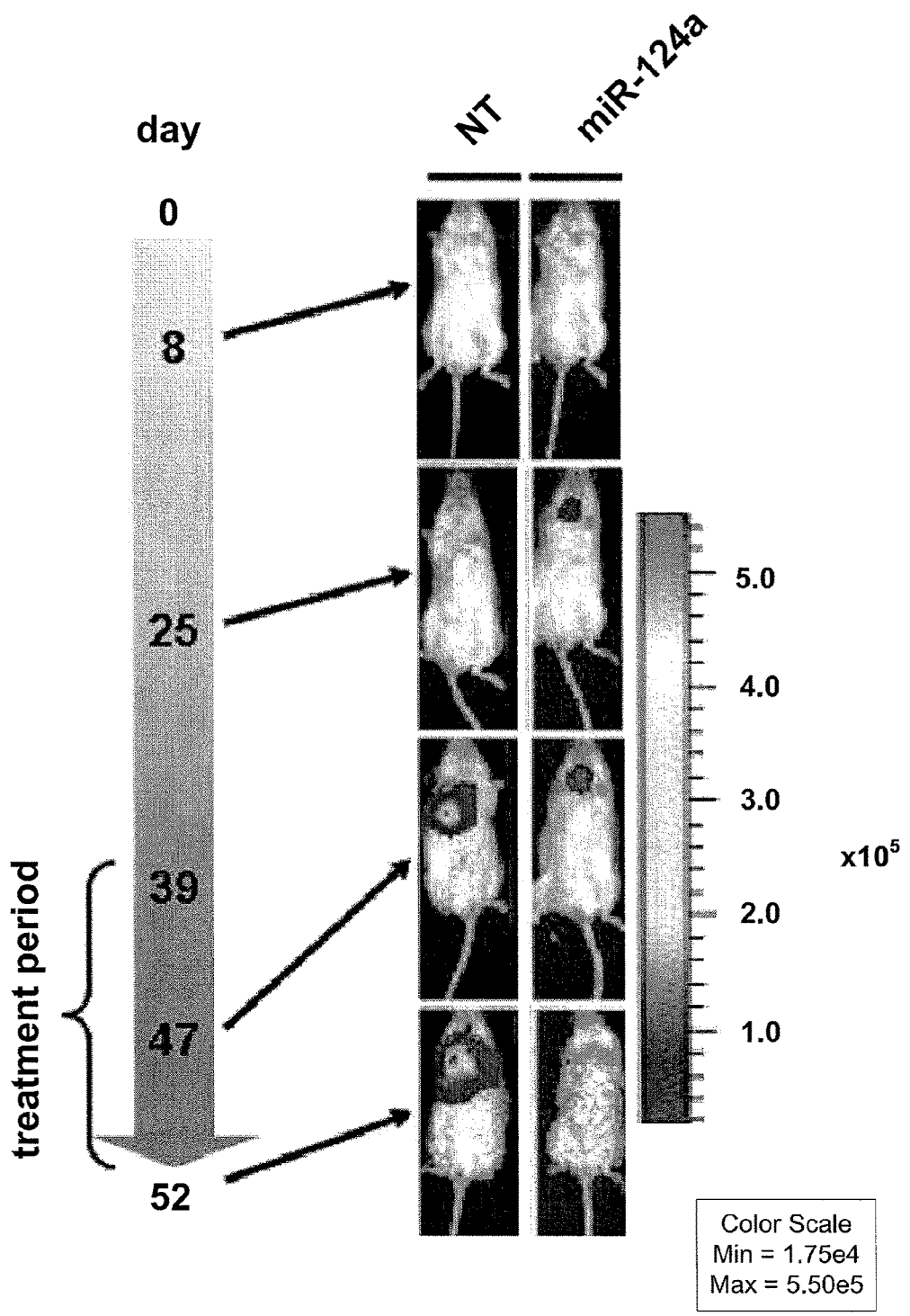
FIG. 14 demonstrates systemic delivery of PORE-formulated therapeutic miRNA to orthotopically grown lung tumors in mice. A mouse carrying an orthotopic lung tumor xenograft received PORE-formulated hsa-miR-124a by systemic administration every 2 days on days 39 through 52. As a reference for normal tumor growth, a mouse without treatment was used. IVIS® data are shown either as images on whole mice (FIG. 14A) or as a quantification expressed in total flux units (FIG. 14B).
Figure 14B:
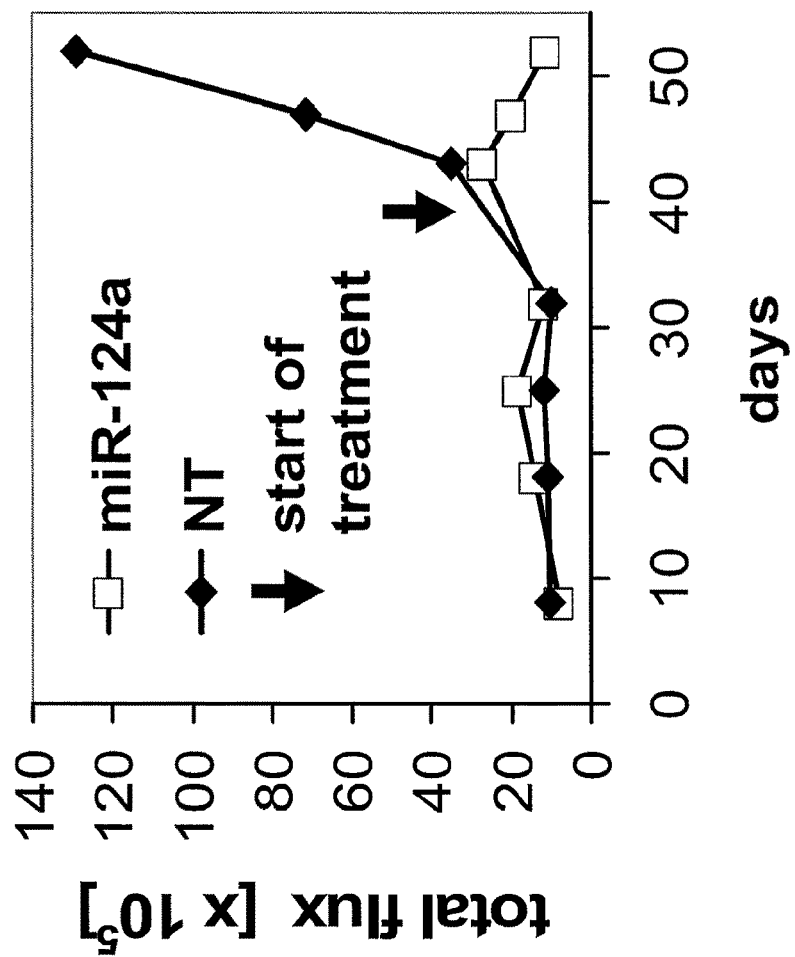

As expected, the non-treated mouse displayed a steady increase of luminescence over time, indicating ongoing H460 tumor growth in lung (NT, FIG. 14). In contrast, the mouse systemically treated with PORE-formulated hsa-miR-124a showed remission of the lung tumor, soon after the first injection with the therapeutic miRNA. According to luminescence data, the tumor volume of the hsa-miR-124a treated mouse was 0.22% of the tumor volume of the non-treated mouse. The data show that PORE facilitated the successful delivery of therapeutic hsa-miR-124a into tumor cells, in an amount that is sufficient to induce a therapeutic response in a lung tumor that is grown at the naturally occurring site.

Example 13

PORE Emulsions in the Systemic Delivery of siRNA In Vivo

Formulations comprising the oils/waxes and neutral lipids effect the systemic delivery to tumor cells in the animal. DOPC, DOPE and DPPE are used as the neutral lipid in the formulation and squalene, coconut oil, steedman's wax, palm oil, bees wax, hemp seed oil, flax oil, omega-3-fish oil, vegetable oil and olive oil are used as the oils and waxes. Components that remain constant are ascorbic acid and Tween 20. The lipid component is mixed with 100 µg RNAi agent in 200 µl phosphate-buffered saline (PBS). A detailed outline of compositions is described in Tables 2-4. Formulations are prepared following the experimental protocol as described in Example 1.

TABLE 2

Compositions of DOPC-based oil emulsions using various oils and waxes.

| Components | variant 1 | variant 2 | variant 3 | variant 4 | variant 5 | variant 6 | variant 7 | variant 8 | variant 9 | variant 10 |
|---|---|---|---|---|---|---|---|---|---|---|
| Ascorbic acid 10 mg/ml | 10 ul | 10 ul | 10 ul | 10 ul | 10 ul | 10 ul | 10 ul | 10 ul | 10 ul | 10 ul |
| Squalene: 100% | 3 ul | N/A | N/A | N/A | N/A | N/A | N/A | N/A | N/A | N/A |
| DOPC: 20 mg/ml | 50 ul | 50 ul | 50 ul | 50 ul | 50 ul | 50 ul | 50 ul | 50 ul | 50 ul | 50 ul |
| Tween 20: 100% | 50 ul | 50 ul | 50 ul | 50 ul | 50 ul | 50 ul | 50 ul | 50 ul | 50 ul | 50 ul |
| Coconut oil | N/A | 3 ul | N/A | N/A | N/A | N/A | N/A | N/A | N/A | N/A |
| Steedmans wax | N/A | N/A | 3 ul | N/A | N/A | N/A | N/A | N/A | N/A | N/A |
| Palm oil | N/A | N/A | N/A | 3 ul | N/A | N/A | N/A | N/A | N/A | N/A |
| bees wax | N/A | N/A | N/A | N/A | 3 ul | N/A | N/A | N/A | N/A | N/A |
| hemp seed oil | N/A | N/A | N/A | N/A | N/A | 3 ul | N/A | N/A | N/A | N/A |
| flax oil | N/A | N/A | N/A | N/A | N/A | N/A | 3 ul | N/A | N/A | N/A |
| Omega-3-Fish | N/A | N/A | N/A | N/A | N/A | N/A | N/A | 3 ul | N/A | N/A |
| Veg oil | N/A | N/A | N/A | N/A | N/A | N/A | N/A | N/A | 3 ul | N/A |
| Olive oil | N/A | N/A | N/A | N/A | N/A | N/A | N/A | N/A | N/A | 3 ul |

Abbreviations:
N/A, not added

TABLE 3

Compositions of DOPE-based oil emulsions using various oils and waxes.

| Components | variant 1 | variant 2 | variant 3 | variant 4 | variant 5 | variant 6 | variant 7 | variant 8 | variant 9 | variant 10 |
|---|---|---|---|---|---|---|---|---|---|---|
| Ascorbic acid 10 mg/ml | 10 ul | 10 ul | 10 ul | 10 ul | 10 ul | 10 ul | 10 ul | 10 ul | 10 ul | 10 ul |
| Squalene: 100% | 3 ul | N/A | N/A | N/A | N/A | N/A | N/A | N/A | N/A | N/A |
| DOPE: 20 mg/ml | 50 ul | 50 ul | 50 ul | 50 ul | 50 ul | 50 ul | 50 ul | 50 ul | 50 ul | 50 ul |
| Tween 20: 100% | 50 ul | 50 ul | 50 ul | 50 ul | 50 ul | 50 ul | 50 ul | 50 ul | 50 ul | 50 ul |
| Coconut oil | N/A | 3 ul | N/A | N/A | N/A | N/A | N/A | N/A | N/A | N/A |
| Steedmans wax | N/A | N/A | 3 ul | N/A | N/A | N/A | N/A | N/A | N/A | N/A |
| Palm oil | N/A | N/A | N/A | 3 ul | N/A | N/A | N/A | N/A | N/A | N/A |
| bees wax | N/A | N/A | N/A | N/A | 3 ul | N/A | N/A | N/A | N/A | N/A |
| hemp seed oil | N/A | N/A | N/A | N/A | N/A | 3 ul | N/A | N/A | N/A | N/A |
| flax oil | N/A | N/A | N/A | N/A | N/A | N/A | 3 ul | N/A | N/A | N/A |
| Omega-3-Fish | N/A | N/A | N/A | N/A | N/A | N/A | N/A | 3 ul | N/A | N/A |
| Veg oil | N/A | N/A | N/A | N/A | N/A | N/A | N/A | N/A | 3 ul | N/A |
| Olive oil | N/A | N/A | N/A | N/A | N/A | N/A | N/A | N/A | N/A | 3 ul |

Abbreviations:
N/A, not added

TABLE 4

Compositions of DPPE-based oil emulsions using various oils and waxes.

| Components | variant 1 | variant 2 | variant 3 | variant 4 | variant 5 | variant 6 | variant 7 | variant 8 | variant 9 | variant 10 |
|---|---|---|---|---|---|---|---|---|---|---|
| Ascorbic acid 10 mg/ml | 10 ul | 10 ul | 10 ul | 10 ul | 10 ul | 10 ul | 10 ul | 10 ul | 10 ul | 10 ul |
| Squalene: 100% | 3 ul | N/A | N/A | N/A | N/A | N/A | N/A | N/A | N/A | N/A |
| DPPE: 20 mg/ml | 50 ul | 50 ul | 50 ul | 50 ul | 50 ul | 50 ul | 50 ul | 50 ul | 50 ul | 50 ul |
| Tween 20: 100% | 50 ul | 50 ul | 50 ul | 50 ul | 50 ul | 50 ul | 50 ul | 50 ul | 50 ul | 50 ul |

TABLE 4-continued

Compositions of DPPE-based oil emulsions using various oils and waxes.

| Components | variant 1 | variant 2 | variant 3 | variant 4 | variant 5 | variant 6 | variant 7 | variant 8 | variant 9 | variant 10 |
|---|---|---|---|---|---|---|---|---|---|---|
| Coconut oil | N/A | 3 ul | N/A | N/A | N/A | N/A | N/A | N/A | N/A | N/A |
| Steedmans wax | N/A | N/A | 3 ul | N/A | N/A | N/A | N/A | N/A | N/A | N/A |
| Palm oil | N/A | N/A | N/A | 3 ul | N/A | N/A | N/A | N/A | N/A | N/A |
| bees wax | N/A | N/A | N/A | N/A | 3 ul | N/A | N/A | N/A | N/A | N/A |
| hemp seed oil | N/A | N/A | N/A | N/A | N/A | 3 ul | N/A | N/A | N/A | N/A |
| flax oil | N/A | N/A | N/A | N/A | N/A | N/A | 3 ul | N/A | N/A | N/A |
| Omega-3-Fish | N/A | N/A | N/A | N/A | N/A | N/A | N/A | 3 ul | N/A | N/A |
| Veg oil | N/A | N/A | N/A | N/A | N/A | N/A | N/A | N/A | 3 ul | N/A |
| Olive oil | N/A | N/A | N/A | N/A | N/A | N/A | N/A | N/A | N/A | 3 ul |

Abbreviations:
N/A, not added

Each $3\times10^6$ human H460 non-small lung cancer cells stably expressing luciferase are mixed with BD Matrigel™, (BD Biosciences; San Jose, Calif., USA; Cat. No. 356237) in a 1:1 ratio and subcutaneously injected into the lower back of NOD/SCID mice (Jackson Laboratories; Bar Harbor, Me., USA). Mice are regularly monitored by an IVIS imaging system (Xenogen, Caliper Life Sciences, Hopkinton, Mass., USA) measuring luminescence (luciferase activity) following an intraperitoneal injection of the luciferase substrate luciferin. After mice develop readily detectable lung tumors, total luminescence data is recorded (total flux, 0 hours). Immediately after measuring luminescence, mice are given intravenous tail-vein injections of 100 µg luciferase-directed siRNA (si-luc) in 200 µl PORE using the compositions described in Tables 2-4. As negative controls, a group of mice receive intravenous injections of PBS. Forty-eight hours after injection of formulated oligonucleotide, luminescence is measured again and expressed as percent change relative to the total flux of each mouse at 0 hours (100%). The extent of luciferase silencing is thus measured.

Example 14

Tween 20 in PORE

Various Tween 20 concentrations in the systemic delivery of siRNA, including ratios of oil:Tween 20 at ranges from 3:0 to 3:100 are described in Table 5. The PORE formulations using these different Tween 20 concentrations are prepared as described in Example 1. Components that are added at constant amounts are ascorbic acid, squalene and DOPC. As described above, the lipid component is mixed with 100 µg RNAi agent in 200 µl PBS.

TABLE 5

Compositions of DOPC-based oil emulsions using various concentrations of Tween 20.

| Components | variant 1 | variant 2 | variant 3 | variant 4 | variant 5 | variant 6 | variant 7 | variant 8 | variant 9 | variant 10 |
|---|---|---|---|---|---|---|---|---|---|---|
| Ascorbic acid 10 mg/ml | 10 ul | 10 ul | 10 ul | 10 ul | 10 ul | 10 ul | 10 ul | 10 ul | 10 ul | 10 ul |
| Squalene: 100% | 3 ul | 3 ul | 3 ul | 3 ul | 3 ul | 3 ul | 3 ul | 3 ul | 3 ul | 3 ul |
| DOPC: 20 mg/ml | 50 ul | 50 ul | 50 ul | 50 ul | 50 ul | 50 ul | 50 ul | 50 ul | 50 ul | 50 ul |
| Tween 20: 100% | N/A | 0.0005 ul | 0.001 ul | 0.01 ul | 0.05 ul | 0.1 ul | 1 ul | 10 ul | 50 ul | 100 ul |

Abbreviations:
N/A, not added

The ability of the formulations described in Table 5 to deliver an RNAi agent in the animal is tested as described in Example 13, using the H460 tumor model stably expressing luciferase and a luciferase-directed siRNA as the RNAi agent. Luminescence is recorded right before i.v. injections of formulated siRNA (0 hrs) and 48 hours thereafter. Luminescence values (total flux) are expressed as percent change relative to the total flux of each mouse at 0 hours (100%).

Example 15

Oils/Waxes and Neutral Lipids Emulsions

Various oils/waxes and neutral lipid PORE formulations listed in Tables 6-8 are prepared, complexed with synthetic miRNA, incubated in plasma, and tested for intact miRNA. The various mixtures shown in Tables 6-8 are mixed, frozen, and dried as described in Example 1. The lipid component is mixed with 100 µg RNAi agent in 200 µl phosphate-buffered saline (PBS).

TABLE 6

Compositions of DOPC-based oil emulsions using various oils and waxes.

| Components | variant 1 | variant 2 | variant 3 | variant 4 | variant 5 | variant 6 | variant 7 | variant 8 | variant 9 | variant 10 |
|---|---|---|---|---|---|---|---|---|---|---|
| Ascorbic acid 10 mg/ml | 10 ul | 10 ul | 10 ul | 10 ul | 10 ul | 10 ul | 10 ul | 10 ul | 10 ul | 10 ul |
| Squalene: 100% | 3 ul | N/A | N/A | N/A | N/A | N/A | N/A | N/A | N/A | N/A |
| DOPC: 20 mg/ml | 50 ul | 50 ul | 50 ul | 50 ul | 50 ul | 50 ul | 50 ul | 50 ul | 50 ul | 50 ul |
| Tween 20: 100% | 50 ul | 50 ul | 50 ul | 50 ul | 50 ul | 50 ul | 50 ul | 50 ul | 50 ul | 50 ul |
| Coconut oil | N/A | 3 ul | N/A | N/A | N/A | N/A | N/A | N/A | N/A | N/A |
| Steedmans wax | N/A | N/A | 3 ul | N/A | N/A | N/A | N/A | N/A | N/A | N/A |
| Palm oil | N/A | N/A | N/A | 3 ul | N/A | N/A | N/A | N/A | N/A | N/A |
| bees wax | N/A | N/A | N/A | N/A | 3 ul | N/A | N/A | N/A | N/A | N/A |
| hemp seed oil | N/A | N/A | N/A | N/A | N/A | 3 ul | N/A | N/A | N/A | N/A |
| flax oil | N/A | N/A | N/A | N/A | N/A | N/A | 3 ul | N/A | N/A | N/A |
| Omega-3-Fish | N/A | N/A | N/A | N/A | N/A | N/A | N/A | 3 ul | N/A | N/A |
| Veg oil | N/A | N/A | N/A | N/A | N/A | N/A | N/A | N/A | 3 ul | N/A |
| Olive oil | N/A | N/A | N/A | N/A | N/A | N/A | N/A | N/A | N/A | 3 ul |

Abbreviations:
N/A, not added

TABLE 7

Compositions of DOPE-based oil emulsions using various oils and waxes.

| Components | variant 1 | variant 2 | variant 3 | variant 4 | variant 5 | variant 6 | variant 7 | variant 8 | variant 9 | variant 10 |
|---|---|---|---|---|---|---|---|---|---|---|
| Ascorbic acid 10 mg/ml | 10 ul | 10 ul | 10 ul | 10 ul | 10 ul | 10 ul | 10 ul | 10 ul | 10 ul | 10 ul |
| Squalene: 100% | 3 ul | N/A | N/A | N/A | N/A | N/A | N/A | N/A | N/A | N/A |
| DOPE: 20 mg/ml | 50 ul | 50 ul | 50 ul | 50 ul | 50 ul | 50 ul | 50 ul | 50 ul | 50 ul | 50 ul |
| Tween 20: 100% | 50 ul | 50 ul | 50 ul | 50 ul | 50 ul | 50 ul | 50 ul | 50 ul | 50 ul | 50 ul |
| Coconut oil | N/A | 3 ul | N/A | N/A | N/A | N/A | N/A | N/A | N/A | N/A |
| Steedmans wax | N/A | N/A | 3 ul | N/A | N/A | N/A | N/A | N/A | N/A | N/A |
| Palm oil | N/A | N/A | N/A | 3 ul | N/A | N/A | N/A | N/A | N/A | N/A |
| bees wax | N/A | N/A | N/A | N/A | 3 ul | N/A | N/A | N/A | N/A | N/A |
| hemp seed oil | N/A | N/A | N/A | N/A | N/A | 3 ul | N/A | N/A | N/A | N/A |
| flax oil | N/A | N/A | N/A | N/A | N/A | N/A | 3 ul | N/A | N/A | N/A |
| Omega-3-Fish | N/A | N/A | N/A | N/A | N/A | N/A | N/A | 3 ul | N/A | N/A |
| Veg oil | N/A | N/A | N/A | N/A | N/A | N/A | N/A | N/A | 3 ul | N/A |
| Olive oil | N/A | N/A | N/A | N/A | N/A | N/A | N/A | N/A | N/A | 3 ul |

Abbreviations:
N/A, not added

TABLE 8

Compositions of DPPE-based oil emulsions using various oils and waxes.

| Components | variant 1 | variant 2 | variant 3 | variant 4 | variant 5 | variant 6 | variant 7 | variant 8 | variant 9 | variant 10 |
|---|---|---|---|---|---|---|---|---|---|---|
| Ascorbic acid 10 mg/ml | 10 ul | 10 ul | 10 ul | 10 ul | 10 ul | 10 ul | 10 ul | 10 ul | 10 ul | 10 ul |
| Squalene: 100% | 3 ul | N/A | N/A | N/A | N/A | N/A | N/A | N/A | N/A | N/A |
| DPPE: 20 mg/ml | 50 ul | 50 ul | 50 ul | 50 ul | 50 ul | 50 ul | 50 ul | 50 ul | 50 ul | 50 ul |
| Tween 20: 100% | 50 ul | 50 ul | 50 ul | 50 ul | 50 ul | 50 ul | 50 ul | 50 ul | 50 ul | 50 ul |
| Coconut oil | N/A | 3 ul | N/A | N/A | N/A | N/A | N/A | N/A | N/A | N/A |
| Steedmans wax | N/A | N/A | 3 ul | N/A | N/A | N/A | N/A | N/A | N/A | N/A |
| Palm oil | N/A | N/A | N/A | 3 ul | N/A | N/A | N/A | N/A | N/A | N/A |
| bees wax | N/A | N/A | N/A | N/A | 3 ul | N/A | N/A | N/A | N/A | N/A |
| hemp seed oil | N/A | N/A | N/A | N/A | N/A | 3 ul | N/A | N/A | N/A | N/A |

TABLE 8-continued

Compositions of DPPE-based oil emulsions using various oils and waxes.

| Components | variant 1 | variant 2 | variant 3 | variant 4 | variant 5 | variant 6 | variant 7 | variant 8 | variant 9 | variant 10 |
|---|---|---|---|---|---|---|---|---|---|---|
| flax oil | N/A | N/A | N/A | N/A | N/A | N/A | 3 ul | N/A | N/A | N/A |
| Omega-3-Fish | N/A | N/A | N/A | N/A | N/A | N/A | N/A | 3 ul | N/A | N/A |
| Veg oil | N/A | N/A | N/A | N/A | N/A | N/A | N/A | N/A | 3 ul | N/A |
| Olive oil | N/A | N/A | N/A | N/A | N/A | N/A | N/A | N/A | N/A | 3 ul |

Abbreviations:
N/A, not added

The miRNA/lipid/oil emulsions are added to a 10% plasma solution and incubated at room temperature for various time points between 0 and 24 hours. RNA from the samples is recovered using the miRVana RNA Isolation Kit (Ambion) using the manufacturers' recommended procedure for plasma RNA isolation. The resulting RNA samples are subjected to qRT-PCR analysis using a TaqMan® assay for the target miRNA and a second TaqMan® assay for miR-24. The relative abundance of the intact target miRNA in each sample is calculated by subtracting its Ct value from the Ct value of miR-24 from the same sample. The resulting dCt values for each of the samples is compared to a sample in which the target miRNA is incubated in plasma in the absence of an oil/water emulsion to estimate the relative stabilization activities of the various formulations.

Example 16

Tween 20 in PORE

Tween 20 is an emulsifying agent that stabilizes the particles that are formed between the oil, lipid, and RNAi agent. Tween 20 at final concentrations in the complexing solution ranging from 0-50% are described in Table 9. The PORE formulations using these different Tween 20 concentrations are prepared as described in Example 1. Components that are added at constant amounts are ascorbic acid, squalene and DOPC. As described above, the lipid component is mixed with 100 μg RNAi agent in 200 μl PBS.

Example 17

Association of RNAi Agent with PORE

A PORE with 1 mg DOPC, 3 ul squalene, 49 ul Tween 20, and 100 ug of siRNA was prepared using the method described in Example 1. The PORE was added to a 30,000 nominal molecular weight limit filter unit (Millipore corp., Billerica, Mass.) and centrifuged at 10,000×g for 10 min at RT. In separate tubes, the flow-through and trapped materials were recovered and mixed with SYBR Gold (Invitrogen) that had been diluted 100,000-fold with TE (pH 7.5). The solutions were incubated for 5 minutes at room temperature and then assessed for fluorescence by activating the dye using light at a wavelength of 470 nm and a readout at 550 nm. 80% of the siRNA was retained by the filters in the PORE formulation while less than 10% siRNA was retained in the absence of the PORE. This demonstrates that the RNAi agent is associated with the particles formed by the lipid and oil in the formulation.

Example 18

Association of RNAi Agent with PORE Containing Varying Amounts of Tween 20

PORE formulations containing varying amounts of Tween 20 (Table 9, Example 16) are prepared according to Example 1. The amount of RNAi agent associated with each PORE

TABLE 9

Compositions of DOPC-based oil emulsions using various concentrations of Tween 20.

| Components | variant 1 | variant 2 | variant 3 | variant 4 | variant 5 | variant 6 | variant 7 | variant 8 | variant 9 | variant 10 |
|---|---|---|---|---|---|---|---|---|---|---|
| Ascorbic acid 10 mg/ml | 10 ul | 10 ul | 10 ul | 10 ul | 10 ul | 10 ul | 10 ul | 10 ul | 10 ul | 10 ul |
| Squalene: 100% | 3 ul | 3 ul | 3 ul | 3 ul | 3 ul | 3 ul | 3 ul | 3 ul | 3 ul | 3 ul |
| DOPC: 20 mg/ml | 50 ul | 50 ul | 50 ul | 50 ul | 50 ul | 50 ul | 50 ul | 50 ul | 50 ul | 50 ul |
| Tween 20: 100% | N/A | 0.01 ul | 0.033 ul | 0.1 ul | 0.33 ul | 1 ul | 3.3 ul | 10 ul | 33 ul | 100 ul |

Abbreviations:
N/A, not added

The ability of the formulations described in Table 9 to stabilize a synthetic miRNA in plasma is measured as described in the example above. To assess active particles maintenance over time, the various complexes are incubated for 0-24 hours at room temperature prior to adding plasma. Stability over 1 week, 1 month, 3 months, 6 months, and 1 year is assessed.

formulation is measured using the column filtration and SYBR Gold quantification protocol described in Example 17.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A composition for the in vivo delivery of an RNAi agent, comprising an emulsion of a lipid component, an aqueous component, and a non-ionic surfactant, wherein
the lipid component comprises 20-40% by weight of a neutral phospholipid and 60-80% by weight of an oil or wax, and wherein the percentage by weight of neutral phospholipid and the percentage by weight of oil or wax totals 100% of the lipid component;
the aqueous component comprises an RNAi agent in an aqueous medium, wherein the RNAi agent is less than 200 nucleotides in length; and
the surfactant comprises 0.1-50% of the total emulsion by weight; wherein the composition does not comprise a cationic lipid.

2. The composition of claim 1, wherein the neutral phospholipid is 1,2-dioleoyl-sn-glycero-3-phosphocholine.

3. The composition of claim 1 or 2, wherein the oil is squalene.

4. The composition of claim 3, wherein the surfactant is polysorbate 20.

5. The composition of claim 3, wherein the RNAi agent is a miRNA.

6. The composition of claim 3, wherein the RNAi agent is an siRNA.

7. The composition of claim 1, further comprising an antioxidant.

8. The composition of claim 1, wherein the surfactant comprises 40-50% of the total emulsion by weight.

9. A method of making an emulsion comprising the steps of:
 a. mixing a neutral phospholipid, an oil, and a non-ionic surfactant in an organic solvent;
 b. evaporating the organic solvent to form a dried lipid component; and
 c. mixing the lipid component with an RNAi agent in an aqueous medium;
wherein
the lipid component comprises 20-40% by weight of a neutral phospholipid and 60-80% by weight of an oil or wax and wherein the percentage by weight of neutral phospholipid and the percentage by weight of oil or wax totals 100% of the lipid component;
the RNAi component comprises an RNAi agent in an aqueous medium, wherein the RNAi agent is less than 200 nucleotides in length; and
the surfactant comprises 0.1-50% of the total emulsion by weight,
wherein the emulsion does not comprise a cationic lipid.

10. The method of claim 9, wherein the neutral phospholipid is 1,2-dioleoyl-sn-glycero-3-phosphocholine.

11. The method of claim 9 or 10, wherein the oil is squalene.

12. The method of claim 11, wherein the surfactant is polysorbate 20.

13. The method of claim 11, wherein the RNAi agent is a miRNA.

14. The method of claim 11, wherein the RNAi agent is an siRNA.

15. The method of claim 9, wherein lipid component comprises 20-40% phospholipid and 60-80% oil or wax; and the surfactant comprises 40-50% of the total emulsion by weight.

16. The method of claim 9, wherein the evaporating is performed by lyophilization.

17. The method of claim 9, wherein the mixing in step c is performed by sonication.

18. The method of claim 9, further comprising extruding the mixture formed in step c.

19. The method of claim 9, further comprising adding an antioxidant to the mixture of step a.

20. A method of delivering an RNAi agent to an animal, comprising administering the composition of claim 1 to the animal.

21. The method of claim 20, wherein the composition is administered by injection.

22. The method of claim 21, wherein the composition is administered systemically.

23. The method of claim 21, wherein the RNAi agent is a miRNA.

24. A composition comprising an emulsion of a lipid component, an aqueous component, and a non-ionic surfactant, wherein
the lipid component comprises 20-40% by weight of a neutral phospholipid and 60-80% by weight of an oil or wax, and wherein the percentage by weight of neutral phospholipid and the percentage by weight of oil or wax totals 100% of the lipid component;
the aqueous component comprises an anti-miRNA agent in an aqueous medium; and
the surfactant comprises 0.1-50% of the total emulsion by weight; wherein the composition does not comprise a cationic lipid.

25. A composition comprising an emulsion of a lipid component, an aqueous component, and a non-ionic surfactant, wherein
the lipid component comprises 20-40% by weight of a neutral phospholipid and 60-80% by weight of an oil or wax, and wherein the percentage by weight of neutral phospholipid and the percentage by weight of oil or wax totals 100% of the lipid component;
the aqueous component comprises an aptamer in an aqueous medium; and
the surfactant comprises 0.1-50% of the total emulsion by weight; wherein the composition does not comprise a cationic lipid.

26. A composition for the in vivo delivery of an RNAi agent, comprising an emulsion of a lipid component, an aqueous component, and polysorbate 20, wherein
the lipid component comprises 20-40% by weight of 1,2-dioleoyl-sn-glycero-3-phosphocholine and 60-80% by weight of squalene, and wherein the percentage by weight of 1,2-dioleoyl-sn-glycero-3-phosphocholine and the percentage by weight of squalene totals 100% of the lipid component;
the aqueous component comprises an RNAi agent in an aqueous medium, wherein the RNAi agent is less than 200 nucleotides in length; and
the polysorbate 20 comprises 0.1-50% of the total emulsion by weight; wherein the composition does not comprise a cationic lipid.

27. The composition of claim 26, wherein the polysorbate 20 comprises 40-50% of the total emulsion by weight.

28. A composition for the in vivo delivery of an RNAi agent, comprising an emulsion of a lipid component, an aqueous component, and a non-ionic surfactant, wherein
the lipid component comprises a neutral phospholipid and an oil or wax, wherein the ratio of neutral phospholipid to oil or wax is from 1:2 to 1:6, and wherein the lipid component comprises only neutral phospholipid and oil or wax;

the aqueous component comprises an RNAi agent in an aqueous medium, wherein the RNAi agent is less than 200 nucleotides in length; and the surfactant comprises 0.1-50% of the total emulsion by weight; wherein the composition does not comprise a cationic lipid.

29. The composition of claim 28, wherein the neutral phospholipid is 1,2-dioleoyl-sn-glycero-3-phosphocholine, the oil or wax is squalene, and the surfactant is polysorbate 20.

* * * * *